(12) United States Patent
Schulz et al.

(10) Patent No.: US 9,952,153 B2
(45) Date of Patent: Apr. 24, 2018

(54) TRANSFORMATION OF MATERIAL INTO AN OPTICALLY MODULATING STATE VIA LASER RADIATION

(75) Inventors: Torsten Schulz, Jena (DE); Daniel Weicherding, Jena (DE)

(73) Assignee: ALERE TECHNOLOGIES GMBH, Jena (DE)

( * ) Notice: Subject to any disclaimer, the term of this patent is extended or adjusted under 35 U.S.C. 154(b) by 487 days.

(21) Appl. No.: 13/991,347

(22) PCT Filed: Dec. 2, 2011

(86) PCT No.: PCT/EP2011/071618
§ 371 (c)(1),
(2), (4) Date: Aug. 12, 2013

(87) PCT Pub. No.: WO2012/072795
PCT Pub. Date: Jun. 7, 2012

(65) Prior Publication Data
US 2013/0316334 A1    Nov. 28, 2013

Related U.S. Application Data

(60) Provisional application No. 61/419,605, filed on Dec. 3, 2010.

(51) Int. Cl.
*G01N 15/06* (2006.01)
*G01N 33/00* (2006.01)
(Continued)

(52) U.S. Cl.
CPC .... *G01N 21/6402* (2013.01); *B01L 3/502707* (2013.01); *B41M 5/24* (2013.01);
(Continued)

(58) Field of Classification Search
CPC .......... G01N 15/06; G01N 33/00; G01N 33/48
(Continued)

(56) References Cited

U.S. PATENT DOCUMENTS 5,658,413 A    8/1997  Kaltenbach et al.
7,169,471 B1 *  1/2007  Dreher et al. ................ 428/402
(Continued)

FOREIGN PATENT DOCUMENTS

JP    2001030171 A    2/2001
JP    2001192036 A    7/2001
(Continued)

OTHER PUBLICATIONS

International Search Report of PCT/EP2011/071618.

*Primary Examiner* — Brian J. Sines
(74) *Attorney, Agent, or Firm* — Steptoe & Johnson LLP

(57) ABSTRACT

A method for the transformation of material (e.g. plastic material) into an optically modulating state via laser radiation is described. The optically modulating state may be a state in which light is emitted at a different wavelength than it is absorbed. The plastic material to may be a thermoplastic or elastomeric material, or an organic polymer selected from the group consisting of polyethylene, polypropylene, polystyrene, polycarbonate and polycycloolefin. The laser radiation may comprise the application of an amount of energy of about 0.1 nJoule/µm² to about 100 µJoule/µm² and/or may comprise a radiation of a wavelength of about 355 nm to about 1064 nm. The optically modulating state of the plastic material may absorb light in a wavelength spectrum of about 380 nm to about 540 nm and/or a wavelength spectrum of about 635 nm to about 655 nm. The optically modulating state of the plastic material may emit light in a wavelength spectrum of about 550 nm to about 800 nm. The transformation of the plastic material may comprise the generation of optically modulating elements on the surface of said (Continued)

plastic material, selected from the group comprising geometrical forms, geometrical pattern, spots, dots, lines, circles, squares, characters, symbols, drawings, barcode and datamatrixcode. The material may be used as component for the manufacture of a device, microfluidic device, system, cartridge or instrument. Based on the employment of the material the usability of a device or system and/or of any procedure, function or method carried out with it or in it may be determined and/or controlled.

7 Claims, 10 Drawing Sheets

(51) Int. Cl.
| | |
|---|---|
| *G01N 33/48* | (2006.01) |
| *G01N 21/64* | (2006.01) |
| *G02C 7/02* | (2006.01) |
| *B01L 3/00* | (2006.01) |
| *B41M 5/24* | (2006.01) |
| *B41M 5/26* | (2006.01) |

(52) U.S. Cl.
CPC .............. *B41M 5/26* (2013.01); *B41M 5/267* (2013.01); *G02C 7/021* (2013.01); *B01L 2300/0654* (2013.01); *B01L 2300/168* (2013.01)

(58) Field of Classification Search
USPC .... 422/50, 68.1, 502, 503, 504; 436/43, 180
See application file for complete search history.

(56) References Cited

U.S. PATENT DOCUMENTS

2002/0144738 A1* 10/2002 Unger et al. ................... 137/824
2007/0029294 A1*  2/2007 Peng ......................... 219/121.69

FOREIGN PATENT DOCUMENTS

| WO | 0188525 A1 | 11/2001 |
|---|---|---|
| WO | 2006117692 A1 | 11/2006 |
| WO | 2009029513 A1 | 3/2009 |
| WO | 2009122930 A1 | 10/2009 |

* cited by examiner

TRANSFORMATION OF MATERIAL INTO AN OPTICALLY MODULATING STATE VIA LASER RADIATION

CLAIM FOR PRIORITY

This application claims priority under 35 USC 371 to International Application No. PCT/EP2011/071618, filed on Dec. 2, 2011, which claims priority to U.S. Patent Application No. 61/419,605, filed Dec. 3, 2010, which is hereby incorporated by reference in its entirety.

REFERENCED APPLICATION DATA

This application refers to the International patent applications WO 2008/135564, WO 2009/112594, WO 2005/108604, WO 2008/062048, WO 2008/055915, WO 2009/013321, WO 2010/105802, WO 2007/051861 and WO 2007/051863, which are all herein incorporated by reference in their entirety.

FIELD OF THE INVENTION

The present invention relates to the transformation of material (e.g. plastic material) into an optically modulating state via laser radiation, as well as optically modulating elements and/or material obtained by the application of laser radiation onto or into the material and devices comprising optically modulating material and/or elements.

BACKGROUND

The labeling and marking of material and products is becoming of rising importance in many industrial fields. The labels and marks are predominantly generated using conventional techniques such as printing, stamping, engraving or embossing. Marking via the application of laser radiation has been established as interesting alternative to these techniques since it is rapid, can be applied on non-planar surfaces and is in general durable and abrasion-resistant due to the inscription in the material, in particular plastic material, itself.

Laser marking methods have been described for different materials, in particular for plastics or polymeric materials. The underlying effect is generally based on an interaction between the polymeric matrix of the material or a laser sensitive additive to said material with a laser beam, which generates a high degree of thermal energy at the laser target point. The application of energy is assumed to result in pyrolysis, carbonization and/or ablation of material, leading to macroscopic modifications of the material, which are optically detectable for the human eye. U.S. Pat. No. 6,284,184 discloses a method of laser marking a plastic substrate based on a layered polymeric substrate, which is ablated in order to reveal a differently colored layer underneath. U.S. Pat. No. 4,822,973 discloses a system, in which the laser radiation passes through the surface of a first layer material and becomes absorbed in a second layer material leading to a laser conveyed marking therein.

The described methods are focused on the generation of generally visible labels or modifications on the treated material, which may however not be applicable in situations in which an optical reaction other than optical reflection is required.

There is thus a need for techniques and materials which overcome the shortcomings of the prior art.

SUMMARY OF THE INVENTION

We describe a method for the transformation of plastic material into an optically excitable modulating state, comprising the application of laser radiation to the plastic material. The optically modulating state may be a state in which light is modulated with respect to one or more of its characteristics comprising wavelength, amplitude, direction and/or phase. For instance, in some embodiments light is emitted by the structures at a different wavelength than it is absorbed (e.g. similar to fluorescence or phosphorescence) and/or at a different direction so that modulation of the light other than pure or nearly pure reflection occur.

In a further aspect a use comprises the employment of laser radiation for the transformation of plastic material into an optically modulating state.

The optically modulating state can be a fluorescent or a scattering state or similar to a fluorescent state or comparable to a fluorescent state. The plastic material to be employed in the use or method may be a thermoplastic material or an elastomeric material.

The plastic material to be employed in the use or method may further be an organic polymer selected from the group consisting of polyethylene, polypropylene, polystyrene, polycarbonate and polycycloolefin.

The laser radiation to be employed in the use or method may comprise the application of an amount of energy of about 0.1 nJoule/µm² to about 100 µJoule/µm².

The laser radiation to be employed in the use or method may comprise a radiation of a wavelength of about 355 nm to about 1064 nm.

The optically modulating state of the plastic material may absorb light in a wavelength spectrum of about 380 nm to about 540 nm and/or a wavelength spectrum of about 635 nm to about 655 nm.

The optically modulating state of the plastic material may emit upon excitation light in a wavelength spectrum of about 550 nm to about 800 nm.

The optically modulating state of the plastic material may emit upon excitation light at peak wavelengths of 593 nm and/or 685 nm.

The transformation of the plastic material comprises the generation of optically modulating elements on the surface of said plastic material, selected from the group comprising geometrical forms, geometrical pattern, spots, dots, lines, circles, squares, characters, symbols, drawings, barcode and datamatrixcode, or any combination thereof.

The transformation of the plastic material comprises the generation of optically modulating elements. In some embodiments, said optically modulating elements are geometrical elements, and/or have a diameter of at least 5 µm.

The plastic material to be employed in the use or method may be transparent.

The transformed plastic material may be water-resistant and/or indissoluble.

In another aspect an optically modulating plastic material is produced by a method as described herein.

The produced plastic material may comprise a datamatrix of optically modulating spot elements.

The produced plastic material may additionally or alternatively comprise optically modulating reference marks for the alignment of arrays or array components.

In another aspect a method for marking the surface of a material comprises applying laser radiation to the material, wherein said marked surface is optically modulating.

The laser radiation to be employed in the method comprises the application of an amount of energy of about 0.1 nJoule/μm² to about 100 μJoule/μm².

The optical excitation of the marked surface may be broadband light excitation.

The broadband light excitation of the marked surface may be an excitation in a wavelength spectrum of about 380 nm to about 540 nm and/or a wavelength spectrum of about 635 nm to about 655 nm.

The marked surface may emit upon excitation light in a wavelength spectrum of about 550 nm to about 800 nm.

The marked surface may emit upon excitation light at peak wavelengths of 593 nm and/or 685 nm.

In another aspect a material is produced by a method for marking the surface of a material.

The material may be a plastic material.

The plastic material may be a thermoplastic material or an elastomeric material.

Or the plastic material may be an organic polymer selected from the group consisting of polyethylene, polypropylene, polystyrene, polycarbonate and polycycloolefin.

In another aspect a material comprises a surface comprising one or more laser marks, wherein said laser mark is optically modulating.

The laser mark may be obtained from the application of laser radiation of an energy of about 0.1 nJoule/μm² to about 100 μJoule/μm².

The laser mark may emit upon excitation light in a wavelength spectrum of about 550 nm to about 800 nm.

The laser mark may emit upon excitation light at peak wavelengths of 593 nm and/or 685 nm.

The excitation may be a broadband light excitation.

The broadband light excitation may be an excitation in a wavelength spectrum of about 380 nm to about 540 nm and/or a wavelength spectrum of about 635 nm to about 655 nm.

The material may be a plastic material.

The plastic material may be a thermoplastic material or an elastomeric material.

Or the plastic material may be an organic polymer selected from the group consisting of polyethylene, polypropylene, polystyrene, polycarbonate and polycycloolefin.

In yet another aspect a datamatrix is composed of or comprises a laser mark on a material, wherein said laser mark is optically modulating.

The laser mark may emit upon excitation light in a wavelength spectrum of about 550 nm to about 800 nm.

The laser mark may emit upon excitation light at peak wavelengths of 593 nm and/or 685 nm.

The excitation may be a broadband light excitation.

The broadband light excitation may be an excitation in a wavelength spectrum of about 380 nm to about 540 nm and/or a wavelength spectrum of about 635 nm to about 655 nm.

The datamatrix may comprise a geometrical form, geometrical pattern, spot, dot, line, circle, square, character, symbol, drawing or barcode or any combination thereof.

In a further aspect a reference mark is composed of or comprises a laser mark on a material, wherein said laser mark is optically modulating.

The excitation may be a broadband light excitation.

The broadband light excitation may be an excitation in a wavelength spectrum of about 380 nm to about 540 nm and/or a wavelength spectrum of about 635 nm to about 655 nm.

The laser mark of the reference mark may be or may comprises a geometrical form, geometrical pattern, spot, dot, line, circle, square, character, symbol, drawing, or barcode or any combination thereof.

The reference mark may be an alignment mark.

The alignment mark may be an array alignment mark.

In another aspect material as described herein is used as component for the manufacture of a device or instrument.

In a further aspect a method for the manufacture of a device or components thereof comprises the step of transforming material or a part of the material of said device into an optically modulating state by the application of laser radiation to said material.

The material may be plastic material.

The device to be produced may comprises a first channel having an inlet opening, and a longitudinal section in fluid communication with the inlet opening.

The device to be produced may comprises a first channel having an inlet opening, an outlet, and a longitudinal section between said inlet opening and said outlet, a channel including a capillary inlet; and a detection region in fluid communication with the capillary inlet.

The device to be produce may be a device for qualitatively and/or quantitatively detecting molecular interactions between probe molecules and target molecules, comprising:

a micro-array comprising probe molecules immobilized in array elements, said micro-array being disposed on a first surface of the device; and a reaction chamber formed between the first surface including the micro-array disposed thereon, and a second surface.

The device to be produced may comprise first and second substrates defining a channel therebetween, at least one of the substrates being flexible, the channel comprising an array of spaced-apart test zones, each test zone comprising a probe compound configured to participate in an assay for a target analyte.

The device to be produced may comprise a reaction chamber formed within a chamber body between a first surface and a second surface.

The device to be produced may comprise a reaction chamber formed within a chamber body between a first surface and a second surface, wherein the second surface is located opposite to the first surface, wherein the distance between the first surface and the second surface is variable at least in one or more parts of the surface area of the first surface and/or the second surface.

The device to be produced may comprise:

a cartridge having a microfluidic channel including a capillary inlet; and a detection region in fluid communication with the capillary inlet;

a microfluidic flow path having an at least partially deformable wall and in fluid communication with the detection region of the channel; and a control element.

In another aspect the material as described herein is used for controlling optical parameters.

The optical parameter may be the focus of an optical device.

In another aspect a microfluidic device comprises:

a first channel having an inlet opening, and a longitudinal section in fluid communication with the inlet opening wherein said device is at least partially composed of or comprises plastic material transformed into an optically modulating state.

In another aspect a microfluidic device comprises:

a first channel having an inlet opening, an outlet, and a longitudinal section between said inlet opening and said outlet, a channel including a capillary inlet; and a detection region in fluid communication with the capillary inlet, wherein said device is at least partially composed of or comprises plastic material transformed into an optically modulating state.

In another aspect a device for qualitatively and/or quantitatively detecting molecular interactions between probe molecules and target molecules, comprises:

a micro-array comprising probe molecules immobilized in array elements, said micro-array being disposed on a first surface of the device; and a reaction chamber formed between the first surface including the micro-array disposed thereon, and a second surface, wherein said device is at least partially composed of or comprises plastic material transformed into an optically modulating state.

The distance between said micro-array and the second surface may be variable.

In another aspect a cartridge has a micro fluidic channel including a capillary inlet and a detection region in fluid communication with the capillary inlet, wherein said cartridge is at least partially composed of or comprises plastic material transformed into an optically modulating state.

In another aspect a device comprises:

first and second substrates defining a channel therebetween, at least one of the substrates being flexible, the channel comprising an array of spaced-apart test zones, each test zone comprising a probe compound configured to participate in an assay for a target analyte, wherein said device is at least partially composed of or comprises plastic material which comprises one or more optically modulating elements.

In another aspect a device for the qualitative and/or quantitative detection of particles comprises:

a reaction chamber formed within a chamber body between a first surface and a second surface, wherein said device is at least partially composed of or comprises plastic material transformed into an optically modulating state.

In another aspect a device for the qualitative and/or quantitative detection of particles comprises:

a reaction chamber formed within a chamber body between a first surface and a second surface, wherein the second surface is located opposite to the first surface, and a microfluidic flow path having an at least partially deformable wall, being in fluid communication with the reaction chamber, wherein said device is at least partially composed of or comprises plastic material transformed into an optically modulating state.

The device may comprise one or more optically modulating elements located on either the first or the second surface of the reaction chamber.

In another aspect a device for detecting an analyte comprises a cartridge having:

a microfluidic channel including an inlet and a detection region in fluid communication with the inlet;

a microfluidic flow path having an at least partially deformable wall and in fluid communication with the detection region of the channel; and a cap comprising: a sealing member configured to seal with the inlet and form a fluid circuit including the inlet, the microfluidic channel and the microfluidic flow path and wherein said device is at least partially composed of or comprises plastic material transformed into an optically modulating state.

In yet another aspect a system for detecting an analyte, comprising a cartridge has:

a microfluidic channel including an inlet and a detection region in fluid communication with the inlet;

a microfluidic flow path having an at least partially deformable wall and in fluid communication with the detection region of the channel; and a cap comprising:

a sealing member configured to seal with the inlet and form a fluid circuit including the inlet, the microfluidic channel and the microfluidic flow path; and a fluorescence detector including:

a light source;

a condenser lens; and an objective lens;

wherein said system is at least partially composed of or comprises plastic material transformed into an optically modulating state.

In a further aspect a device for detecting an analyte in a sample, comprises: a cartridge having:

a microfluidic channel including a capillary inlet; and a detection region in fluid communication with the capillary inlet;

a microfluidic flow path having an at least partially deformable wall and in fluid communication with the detection region of the channel; and a control element, wherein said control element is at least partially composed of or comprises plastic material transformed into an optically modulating state.

The material of the device or of the cartridge or of the system may comprise one or more optically modulating elements.

The material of the device or of the cartridge or of the system may comprise an array of optically modulating spots.

The material of the device or of the cartridge or of the system may comprise a datamatrix or a reference mark.

The material of the device or of the cartridge or of the system may comprise a datamatrix as described herein.

The material of the device or of the cartridge or of the system may comprise a reference mark as described herein.

The material of the device or of the cartridge or of the system may at least partially be composed of or comprises material as described herein.

In another aspect a method for the qualitative and/or quantitative detection of particles, comprises:

positioning a sample supposed to comprise one or more species of particles to be detected in a reaction chamber comprised in a device as described herein;

displacing at least a part of the sample within the reaction chamber via the one or more displacers; and detecting/determining a value indicative for the presence and/or number of one or more species of particles.

In another aspect a method comprises labeling particles immobilized in the microfluidic channel of a device or system with an optical label or labeling reagent;

obtaining a first image comprising at least a subset of the immobilized particles;

determining a first value indicative for the number of particles in the first image;

obtaining a further image of the subset of immobilized particles after an interim;

determining a further value indicative for the number of particles in the further image;

determining a third value indicative for the activity and/or quality of the optical label or labeling reagent and/or the quality of an interaction between a particle and a labeling reagent and/or the usability of the device or system and/or of any procedure, function or method carried out with or in said device or system and/or the accuracy of a test result obtained by using said device or system, based on a comparison of the first value and the further value, and using before, between and/or after these steps control elements for focusing and/or aligning said images, wherein said control element is at least partially composed of or comprises plastic material transformed into an optically modulating state.

In yet another aspect a method comprises:

providing a device or system comprising plastic material transformed into an optically modulating state wherein said material comprises a predetermined number of optically modulating elements and/or comprises optically modulating elements of a predetermined size;

obtaining an image comprising at least a subset of the optically modulating elements;

determining the number and/or size of the optically modulating elements comprised in said image;

determining a value indicative for the usability of the device or system and/or of any procedure, function or method carried out with or in said device or system and/or the accuracy of a test result obtained by using said device or system, based on a comparison of the determined number and/or size of the optically modulating elements, with said predetermined number and/or size.

The method may additionally comprise:

positioning a sample supposed to comprise one or more species of particles to be detected in a reaction chamber comprised in the device; and detecting/determining a value indicative for the presence and/or number of one or more species of particles.

The method may further comprise displacing at least a part of the sample within the reaction chamber via one or more displacers.

The material may comprise an array of optically modulating spots.

The device or system may at least partially be composed of or comprise material as described herein.

The particle to be detected or immobilized in a device or method may be a prokaryotic cell, a eukaryotic cell, or a viral particle.

The particle to be detected or immobilized in a device or method may be a CD4+ T-cell.

BRIEF DESCRIPTION OF THE DRAWINGS

FIG. 2A depicts spots with a pitch of 40-45 µm illuminated with the visible light spectrum. The image was taken with a standard microscope at 2× magnification. FIG. 2B depicts the same spots illuminated with light of a wavelength of 520 nm. The image was taken with PIMA analyzer.

FIG. 3A depicts spots with a diameter of 25-30 µm illuminated with the visible light spectrum. The image was taken with a standard microscope at 2× magnification. FIG. 3B depicts the same spots illuminated with light of a wavelength of 520 nm. The image was taken with PIMA analyzer.

FIG. 4A depicts the spots at a 100× magnification. FIG. 4B, FIG. 4C, FIG. 4D and FIG. 4E show different spot morphologies. The spot morphology is dependent on the energy input.

FIGS. 8A and B show the surface of the channel comprising the structures in an optically modulating state imaged by a PIMA Analyzer. In FIG. 8A, the image was detected at a wavelength of 593 nm and an exposure time of 300 ms and a master gain of 2.74, while the image shown in FIG. 8B was detected at 685 nm with a exposure time of 300 ms and a master gain factor of 11.68.

DETAILED DESCRIPTION

Figure 1:
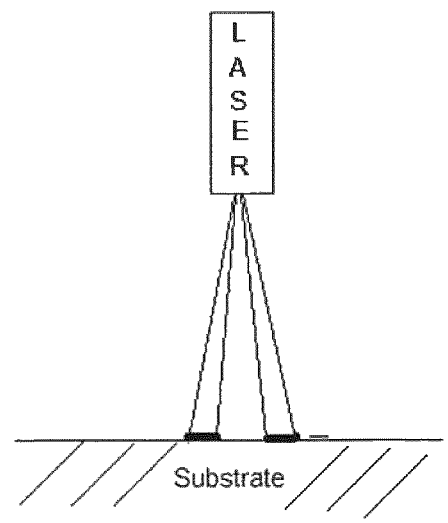
FIG. 1 illustrates the marking of a material by laser radiation.

A method for the transformation of plastic material into an optically modulating state, comprises the application of laser radiation to plastic material.

The "transformation" can be a modification of the surface of the material, e.g. plastic material and/or a modification of one or more layers underneath the surface of the material, e.g. in cases in which layers of different transmissibility are present in the material. In some embodiments the transformation may be a locally limited strong increase in temperature leading to structural and/or chemical modifications of the material, e.g. plastic material, for instance pyrolysis of the material, carbonization of the material, generation of aromatic structures in the material, generation of ablated regions, generation of craters, scratches, holes, embossments or rims. In some embodiments the modification may take place in specific, predetermined regions or layers of the material, e.g. plastic material, due to the presence of additives, e.g. laser-sensitive additives, or due to the presence of transmissible outer layers in the material, e.g. plastic material. In further embodiments the transformation may have a superficial or essentially planar or essentially two dimensional effect. In other embodiments the transformation may have a spatial or essentially three dimensional effect. An example of a spatial or essentially three dimensional effect is the modification of material into relief forms, or the modification of transparent material into a holographic, three dimensional form.

The material to be transformed can be any suitable material. Suitable material is any material which can be modified structurally and/or chemically, e.g. via pyrolysis, carbonization, generation of aromatic structures, generation of craters, scratches, holes, embossments or rims. In some embodiments the material is plastic material. Plastic material can be a natural, synthetic or semi-synthetic organic solid, e.g. a polymer of high molecular mass, which may or may not contain other substances to improve performance. The plastic material can be soft, thermoset, elastomeric, biodegradable, electrically conductive, impervious to water or have further or other properties.

The transformation method leads to an optically modulating state of the treated material, e.g. plastic material. An "optically modulating state" as used herein can be a state in which the wavelength of the light is changed and/or in which the direction of light radiation or reflection is changed. In an "optically modulating state" light may be emitted by the modified point or region of the material, e.g. plastic material, at a different wavelength than it is absorbed. In some embodiments the emitted light may have a longer wavelength, and therefore lower energy, than the absorbed radiation. The wavelength of the absorbed light, the wavelength of the emitted light and/or the duration of the light emission after the absorption may vary. In some embodiments the optically modulating state may be similar to or comparable to a fluorescent state in which the emitted light has a longer wavelength, than the absorbed radiation and wherein the light emission stops shortly after the light absorption stops. For example, if the treated material in an optically modulating state is excited with a light of a wavelength in a range of about 350 to 750 nm, it may emit light of a longer wavelength, respectively, in a range of about 360 to 850 nm. In other embodiments the optically modulating state may be similar to or comparable to a phosphorescent state in which the emitted light has a longer wavelength, than the absorbed radiation and wherein the light emission continues after the light absorption has stopped. The optically modulating state may in certain, specific situations also be similar to or at least partially comprise a state in which modifications of the light other than pure or nearly pure reflection occurs, e.g. states in which incoming or impinging light is scattered. The optically modulating state may further be a fluorescent state.

The laser radiation to be applied for the method can be any suitable laser radiation, e.g. ranging from wavelengths of 157 nm to 1064 nm. In some embodiments the laser radiation is strong enough to cause evaporation, vaporization or melting of the impinged material. In some embodiments, the laser radiation is obtained from commercially available lasers. Examples include YAG lasers. The specific type of laser may be a function of the material to be processed, of the envisaged temperature, of the envisaged modification type etc. Suitable laser forms, methods and apparatuses are known to the person skilled in the art. In one embodiment the laser radiation to be applied is derived from a solid state neodymium yttrium aluminium garnet (Nd:YAG) laser. In another embodiment the laser radiation to be applied is derived from a solid state neodymium:yttrium vanadide (Nd:YVO$_4$) laser. The power rating of the laser apparatuses may in some embodiments vary between about 1 W and 6 W, e.g. be at 0.5, 1, 2 W, 3 W, 4 W, 5 W or 6 W. The power may be adjusted via laser diodes. The laser diodes may be set to transmission of between about 1% to about 99%, e.g. to about 10%, 15%, 20%, 25%, 26%, 27%, 28%, 29%, 30%, 31%, 32%, 33%, 34%, 35%, 40%, 45%, 50%, 55%, 60%, 70%, 80%, 90% or more.

The application of the laser radiation may be performed continuously or periodically, e.g. in the form of pulses. The application form and/or time may be set with regard to the degree of modification, the material to be treated, the laser model, the used wavelength and further suitable parameters known to the person skilled in the art. Examples of application times are ranges of about 0.05 μs to 1 seq, 0.1 μs to 0.5 sec, 1 μs to 0.1 sec, 2 μs, 3 μs, 4 μs, 5 μs, 6 μs, 7 μs, 8 μs, 9 μs, 10 μs, 20 μs, 30 μs, 50 μs, 100 μs, 200 μs, 300 μs, 400 μs, 500 μs, 600 μs, 700 μs, 800 μs, 900 μs, 1 ms, 10 ms, 100 ms. The application times may be given in the form of laser radiation pulses. The pulses may be repeated once, twice, 3 times, 4 times, 5 times, 6 times, 7 times, 8 times, 10 times or more often. The pulses may be followed by pauses or interims of different time periods, e.g. about 1 μs to 10 sec, 2 μs, 3 μs, 4 μs, 5 μs, 6 μs, 7 μs, 8 μs, 9 μs, 10 μs, 20 μs, 30 μs, 50 μs, 100 μs, 200 μs, 300 μs, 400 μs, 500 μs, 600 μs, 700 μs, 800 μs, 900 μs, 1 ms, 10 ms, 100 ms, 1 sec or longer.

In case a pulsed laser radiation is applied, the pulse frequency may be set at about 1 kHz to about 150 kHz, e.g. at about 10 kHz, 15 kHz, 20 kHz, 25 kHz, 30 kHz, 35 kHz, 40 kHz, 45 kHz, 50 kHz, 55 kHz, 60 kHz, 70 kHz, 80 kHz, 100 kHz, 120 kHz, 150 kHz.

The application of the laser radiation may, in another embodiment, be an application onto the material and/or into the material.

The method for the transformation of material, e.g. plastic material, into an optically modulating state may be carried out at a fixed distance between the laser radiation source and the material to be transformed, or at varying distances. The distance may be determined in respect of the type of laser source, the energy to be applied, the form of the envisaged modification etc. In one embodiment, during the application of laser radiation the material to be transformed may be in a fixed position and the laser radiation source may be in a fixed position. In a further embodiment, during the application of laser radiation the material to be transformed may be moved in parallel to the laser radiation source or perpendicularly or axially thereto and the laser radiation source may be in a fixed position. In a further embodiment, during the application of laser radiation the material to be transformed may be in a fixed position and the laser radiation source may be moved in parallel to the material or perpendicularly or axially thereto.

In a further embodiment the outcome of the application of laser radiation may be controlled, e.g. by microscopic inspection, fluorescence microscopic inspection or other suitable inspection techniques known to the person skilled in the art. Depending on the form, amount and/or state of transformation of the material, laser radiation may be applied a second or further time at the same point or region, or any portion thereof.

Accordingly, an advantageous method is provided, which allows the modification of material into an optically modulating state, i.e. into a state in which the impinging light is modified in at least one of its properties such as the wavelength of the emitted light or the direction of the reflected light. The mentioned properties may be obtained and/or adjusted and/or modified via applying laser radiation as indicated above. This method can advantageously be used for a great variety of different applications. Material may be marked superficially, or internally, i.e. in deeper layers without modification of the outermost layer; material may externally or internally be decorated or covered with optically modulating points, symbols, codes, regions etc. whose visibility may depend on the impinging light, e.g. the wavelength of the impinging light; material may be decorated or covered with optically modulating points, symbols, codes, regions etc. which replace previously used optical control elements, e.g. attached entities.

A use of laser radiation for the transformation of material, e.g. plastic material, into an optically modulating state may comprise the employment of laser radiation as described herein for modifications of material, e.g. plastic material, as described herein in order to obtain material in an optically modulating state as described herein.

In a further embodiment, the plastic material to be employed in the use or method as described herein may be a thermoplastic material or an elastomeric material.

"Thermoplastic" as used herein refers to a thermosoftening plastic polymer, which becomes liquid when heated and freezes to a glassy state when cooled sufficiently. The thermoplastic may be a high-molecular-weight polymer whose chains associate through weak Van der Waals forces, stronger dipole-dipole interactions and hydrogen bonding; or stacking of aromatic rings. The thermoplastic material may comprise additional components, e.g. lasersensitive compounds. Examples of thermoplastics include Acrylonitrile butadiene styrene (ABS) Acrylic (PMMA), Celluloid, Cellulose acetate, Cycloolefin Copolymer (COC), Ethylene-Vinyl Acetate (EVA), Ethylene vinyl alcohol (EVOH), Fluoroplastics (PTFE, with FEP, PFA, CTFE, ECTFE, ETFE), Ionomers, acrylic/PVC alloy, Liquid Crystal Polymer (LCP), Polyacetal (POM or Acetal), Polyacrylates (Acrylic), Polyacrylonitrile (PAN or Acrylonitrile), Polyamide (PA), Polyamide-imide (PAI), Polyaryletherketone (PAEK or Ketone), Polybutadiene (PBD), Polybutylene (PB), Polybutylene terephthalate (PBT), Polycaprolactone (PCL), Polychlorotrifluoroethylene (PCTFE), Polyethylene terephthalate (PET), Polycyclohexylene dimethylene terephthalate (PCT), Polycarbonate (PC), Polyhydroxyalkanoates (PHAs), Polyketone (PK), Polyester, Polyethylene (PE), Polyetheretherketone (PEEK), Polyetherketoneketone (PEKK), Polyetherimide (PEI), Polyethersulfone (PES), Polyethylenechlorinates (PEC), Polyimide (PI), Polylactic acid (PLA), Polymethylpentene (PMP), Polyphenylene oxide (PPO), Polyphenylene sulfide (PPS), Polyphthalamide (PPA), Polypropylene (PP), Polystyrene (PS), Polysulfone (PSU), Polytrimethylene terephthalate (PTT), Polyurethane (PU), Polyvinyl acetate (PVA), Polyvinyl chloride (PVC), Polyvinylidene chloride (PVDC), and Styrene-acrylonitrile (SAN).

"Elastomeric material" as used herein refers to a polymer with the property of viscoelasticity, wherein the monomers, which link to form the polymer are typically made of carbon, hydrogen, oxygen and/or silicon. Elastomeric materials may be amorphous polymers existing above their glass transition temperature, so that considerable segmental motion is possible. At ambient temperatures they may be relatively soft and deformable. Examples of elastomeric material include Natural rubber (NR), Synthetic polyisoprene (IR), Butyl rubber (copolymer of isobutylene and isoprene, IIR), Polybutadiene (BR), Styrene-butadiene Rubber (copolymer of polystyrene and polybutadiene, SBR), Nitrile rubber (copolymer of polybutadiene and acrylonitrile, NBR), Hydrogenated Nitrile Rubbers (HNBR), Chloroprene rubber (CR), polychloroprene, Neoprene, EPM (ethylene propylene rubber, a copolymer of ethylene and propylene), Epichlorohydrin rubber (ECO), Polyacrylic rubber (ACM, ABR), Silicone rubber (SI, Q, VMQ), Fluorosilicone Rubber (FVMQ), Fluoroelastomers (FKM, and FEPM) Viton, Tecnoflon, Fluorel, Aflas, Perfluoroelastomers (FFKM) Tecnoflon PFR, Kalrez, Chemraz, Perlast, Polyether block amides (PEBA), Chlorosulfonated polyethylene (CSM), Ethylene-vinyl acetate (EVA), Thermoplastic elastomers (TPE), Elastron, Thermoplastic olefins (TPO), resilin, elastin and Polysulfide rubber.

In a further embodiment the plastic material to be employed in the use or method as described herein may be an organic polymer selected from the group of polyethylene, polypropylene, polystyrene, polycarbonate and polycycloolefin.

"Polyethylene" as used herein refers to a polymeric material composed of long chains of the monomer ethylene. Polyethylene material may be present in different forms of density and/or branching. Examples of polyethylene material include Ultra high molecular weight polyethylene (UHMWPE), i.e. a polyethylene with a molecular weight of between about 3.1 and 5.67 million and densities of about 0.930-0.935 g/cm$^3$; Ultra low molecular weight polyethylene (ULMWPE or PE-WAX); High molecular weight polyethylene (HMWPE); High density polyethylene (HDPE), i.e. a polyethylene with a density of greater or equal to 0.941 g/cm$^3$. and a low degree of branching; High density cross-linked polyethylene (HDXLPE); Cross-linked polyethylene (PEX or XLPE), i.e. a medium- to high-density polyethylene containing cross-link bonds introduced into the polymer structure; Medium density polyethylene (MDPE), i.e. a polyethylene with a density range of 0.926-0.940 g/cm$^3$; Linear low density polyethylene (LLDPE), i.e. a polyethylene with a density range of 0.915-0.925 g/cm$^3$, which is a substantially linear polymer with significant numbers of short branches, commonly made by copolymerization of ethylene with short-chain alpha-olefins; Low density polyethylene (LDPE), i.e. a polyethylene with a density range of 0.910-0.940 g/cm$^3$ which has a high degree of short and long chain branching; Very low density polyethylene (VLDPE), i.e. a polyethylene with a density range of 0.880-0.915 g/cm$^3$, which is a substantially linear polymer with high levels of short-chain branches, commonly made by copolymerization of ethylene with short-chain alpha-olefins.

"Polypropylene" as used herein refers to a thermoplastic polymer composed of monomeric propylene units. Examples of polypropylene include homopolymer polypropylene, random copolymer polypropylene, and block copolymer polypropylene. Propylene may also comprise polypropylene derivatives comprising units of polypropylene and ethylene or polyethylene units.

"Polystyrene" as used herein refers is an aromatic polymer made from the aromatic monomer styrene. Examples of polystyrene include isotactic polystyrene, atactic polystyrene and syndiotactic polystyrene.

"Polycarbonate" as used herein refers to thermoplastic polymers comprising carbonate groups. Polycarbonates may be derived from a combination of bisphenol A and phosgene, a transestrification of bisphenol A and diphenyl carbonate. Polycarbonate material may in one embodiment be transparent.

"Polycycloolefine" as used herein refers to of alkene hydrocarbons, which contain more than one closed ring of carbon atoms, but have no aromatic character. Polycycloolefines may, for example, be composed of monomeric alkenes such as cyclopropene, cyclobutene, cyclopentene, cyclohexene, cycloheptene, cyclohexadiene, 1,4-cyclohexadiene or 1,5-cyclooctadiene.

In a specific embodiment the material is material suitable for the production of optical instruments, e.g. lenses, eyeglasses, sunglasses, contact lenses etc. Examples of such material are materials with a high refraction index, e.g. plastic materials with a high refraction index. The group of plastic materials suitable for the production of optical instruments comprises, for example, polycarbonate plastics such as polyallyldiglycolcarbonat (PADC) or CR-39 or derivatives thereof.

Further plastic materials would be known to the person skilled in the art and/or can be derived from suitable, qualified textbooks, e.g. from Adolf Franck "Kunststoff-Kompendium", Vogel, $6^{th}$ ed., 2006, which is incorporated herein in its entirety.

In a further embodiment the material, e.g. plastic material, may be any combination or juxtaposition of the above mentioned materials, or plastic materials.

In some embodiments the material, e.g. plastic material, to be transformed may comprise one or more additives. An additive may, for example, be a pigment, dye or stain. An example of such colorant additives is carbon black.

Colorant additives may be present in the material, e.g. plastic material in any suitable amount, for example in an amount of about 0.001% to about 25%.

A further additive, which may be present in material, e.g. plastic material, to be transformed, is a lasersensitive compound. The term "laser sensitive compound" as used herein refers to compounds, which are capable of absorbing a higher amount of laser radiation than neighbouring material, leading to locally increased temperatures and subsequent modifications as described herein in said regions or points. Examples of laser sensitive compounds are nanoparticles of a diameter of about 5 nm to 300 nm in at least one dimension, e.g. of a diameter of about 100 nm in at least one dimension. Lasersensitive compounds may be composed of one or more metals or alloys, e.g. nanoparticles comprising such metals or alloys. Examples of suitable metals include aluminium, chrome, zinc, nickel, magnesium, tin, lead, copper, silver, gold, iron, iridium, vanadium, cadmium, titan or platin, or any combination or alloy thereof. In one embodiment, nanoparticles may be present in a range of about 0.01 to about 10% of the material, e.g. plastic material.

A further additive, which may be present in material, e.g. plastic material, to be transformed, may be a lacquer, e.g. a superficially applied lacquer. The lacquer may be in a different color than the material, e.g. plastic material, and/or may convey different properties in comparison to the material underneath. For example, the lacquer may have a different transmissibility for laser radiation, a different wetability, electrical conductivity or electrical chargeability. In a further embodiment, the material, e.g. plastic material may be covered or coated by biological or biochemical compounds, e.g. peptides, proteins, antibodies, nucleic acids, cell portions or fragments, cells, viral fragments etc.

A further additive, which may be present in material, e.g. plastic material, to be transformed is a filler material. Examples of filler material include glass, graphite, $SiO_2$ or $Fe_2O_3$.

In some embodiments the material, e.g. plastic material, to be transformed may be composed of more than one layer, e.g. 2, 3, 4, 5, 6, 7, 9 or 10 layers. The layers may be of different physical composition, different color, different laser radiation transmissibility, different structure, different chemical composition or different durability. For example, the superficial layer may be composed of a transparent material, e.g. a transparent plastic material. Such a material may additionally or alternatively, also have a high transmissibility for laser radiation. The layer underneath may have a nontransparent form and/or comprise lasersensitive compounds, e.g. nanoparticles as described herein. Upon application of laser radiation a modification of the material may only take place in the non-superficial layer.

In certain embodiments, the laser radiation to be applied within the method or uses as described herein, comprises the application of a specific amount of energy per area of the treated material, e.g. plastic material. The term "area of treated material" means the zone or area of material in which the laser radiation impinges. This area excludes neighboring zones or regions, in which no laser radiation impacts. The amount of energy may be between about 0.05 nJoule/$\mu m^2$ to about 150 $\mu$Joule/$\mu m^2$ treated material, e.g. plastic material. In one embodiment, the amount of energy may be between about 0.1 nJoule/$\mu m^2$ to about 100 $\mu$Joule/$\mu m^2$ treated material, e.g. plastic material, e.g. in a range of about 0.5 nJoule/$\mu m^2$ to about 50 $\mu$Joule/$\mu m^2$, a range of about 10 nJoule/$\mu m^2$ to about 25 $\mu$Joule/$\mu m^2$, or a range of about 100 nJoule/$\mu m^2$ to 200 nJoule/$\mu m^2$ treated material. For example, the energy may be at about 150 nJoule/$\mu m^2$ treated material. The amount of energy to be applied may adapted to the material used, the type of modification envisaged, the laser radiation source used, the laser type used, the laser model used or any other suitable parameter known to the person skilled in the art.

In one embodiment, the laser radiation is a laser radiation of a wavelength of about 355 nm to about 1064 nm. The laser radiation may, for example, be of wavelength of about 355 nm to about 500 nm, or of about 500 nm to about 1064 nm. The laser radiation may, for instance, be of a wavelength typical for commercially available lasers, e.g. of about 355 nm, 441.6 nm, 488 nm, 510.5 nm, 514.5 nm, 532 nm, 543.5 nm, 539.5 nm, 594.1 nm, 611.9 nm, 632.8 nm, 647.1 nm, 694.3 nm, 946 nm, or 1064 nm. In another embodiment the laser radiation is a radiation of about 1319 nm. Further examples of suitable wavelengths and/or of suitable lasers to be employed can be derived from a qualified textbook, e.g. from Orazio Svelto: "Principles of Lasers", Springer, $4^{th}$ ed., 1998, which is incorporated herein in its entirety.

The laser radiation of about 355 nm and/or 1064 nm may be obtained in one embodiment from a neodymium:yttrium aluminium garnet (Nd:YAG) laser.

The optically modulating state of the material, e.g. plastic material, may absorb light in a wavelength spectrum of about 380 nm to about 540 nm and/or a wavelength spectrum of about 635 nm to about 655 nm. For example, the material may absorb light at a wavelength of about 380 nm, 390 nm, 400 nm, 410 nm, 420 nm, 430 nm, 440 nm, 450 nm, 460 nm, 470 nm, 480 nm, 490 nm, 500 nm, 510 nm, 520 nm, 530 nm, 540 nm, and/or 630 nm, 635 nm, 640 nm, 645 nm, 650 nm, 655 nm or 660 nm. In some embodiments, the modified material may absorb light in a wavelength spectrum of about 510 nm to about 530 nm. For example, the modified material may absorb light at a wavelength of about 500 nm, 510 nm, 520 nm, 530 nm or 540 nm. The modified material may further absorb light at more than one wavelength, e.g. at two or more of the above indicated wavelengths. The optically modulating state of the plastic material may emit upon excitation, e.g. upon an excitation as described above, light in a wavelength spectrum of about 550 nm to about 800 nm. For example, the material may emit upon excitation light at a wavelength of about 540 nm, 550 nm, 560 nm, 570 nm, 580 nm, 590 nm, 600 nm, 610 nm, 620 nm, 630 nm, 640 nm, 650 nm, 660 nm, 670 nm, 680 nm, 690 nm, 700 nm, 710 nm, 720 nm, 730 nm, 740 nm, 750 nm, 760 nm, 770 nm, 780 nm, 790 nm, 800 nm, or 810 nm. In one embodiment, the modified material may emit upon excitation light at a wavelength of about 593 nm. In a further embodiment, the modified material may emit upon excitation light at a wavelength of about 685 nm. In a further embodiment, the modified material may emit upon excitation light at a wavelength spectrum of about 560 nm to about 660. In a further embodiment, the modified material may emit upon excitation light at a wavelength spectrum of about 660 nm to about 700 nm. The modified material may further emit upon excitation light at more than one wavelength, e.g. at two or more of the above indicated wavelengths. In a further embodiment, the modified material may upon excitation at a wavelength of about 510 nm to about 530 nm emit light at a wavelength of about 560 to 600 nm and/or 660 to 700 nm. The optically modulating state of the plastic material may emit upon excitation light at peak wavelengths of 593 nm and/or 685 nm. The term "peak wavelength" as used herein means a wavelength point around which light emission in a broader spectrum occurs. The transformation of the material, e.g. plastic material, may comprise the generation of optically modulating elements or figures. In one embodiment the optically modulating elements may be generated on the surface of said plastic material. In another embodiment the optically modulating elements may be generated on in a non-surface layer of the material, e.g. a deeper layer of said plastic material. The term "optically modulating element" or "element" as used herein refers to any kind of geometrical form, pattern or picture. Examples of such elements include a spot, dot, line, circle, square, character, a string or combination of characters, any type of symbol or string or combination of symbol. Further envisaged are a drawings, a barcode a datamatrix or a datamatrix code, or any combination of the mentioned elements. An optically modulating element may also have a three dimensional form, e.g. a relief form. Such three dimensional forms may be present at surface layers of the material or in deeper layers of the material.

The optically modulating element may have a diameter in at least one dimension of at least about 5 µm. For example, the element may have a diameter in at least one dimension of at least about 5 µm, 6 µm, 7 µm, 8 µm, 10 µm, 12 µm, 15 µm, 20 µm, 30 µm, 40 µm, 50 µm, 75 µm or 100 µm.

The elements may be present in a density of about 1000 to about 40000 elements per mm$^2$. For instance, the density may be about 1000, 5000, 10000, 20000, 30000, 35000, 40000 elements per mm$^2$.

In one embodiment the average distance between the elements may be about 5 µm, 6 µm, 7 µm, 8 µm, 10 µm, 12 µm, 15 µm, 20 µm, 30 µm, 40 µm, 50 µm, 75 µm or 100 µm.

In another embodiment the elements may be separate elements. In yet another embodiment the elements may be joined elements. "Joined elements" may, for example, comprise a conjunction of neighboring spots forming a line, circle, square, character, symbol etc. Such joined elements may also comprise or be composed of continuous forms obtained by the application of laser radiation as defined above, e.g. grooves or prolonged craters or cuts within the transformed material, e.g. plastic material.

In one embodiment the material, e.g. plastic material, may be transparent. In a further embodiment, the material, e.g. plastic material, may comprise a transparent layer. For example, such transparent material may be composed of or comprise polycarbonate plastics or layers made of polycarbonate plastics. The transparent material may in a further embodiment comprise lasersensitive compounds as defined herein, e.g. nanoparticles.

In a further embodiment the transformed material, e.g. plastic material, i.e. the material being transformed into an optically modulating state may be water-resistant and/or water indissoluble, or be resistant to or indissoluble in other liquids or aqueous solutions. A water-resistant transformed material, e.g. plastic material, may, for example, be useful for applications in wet, aqueous or liquid environments, e.g. in microfluidic devices or cartridges etc. Similarly, water indissoluble material, e.g. plastic material, may for instance be useful in wet, aqueous or liquid environments, e.g. in microfluidic devices or cartridges etc.

In further embodiments, a water-resistant or water indissoluble transformed material may be used for focusing procedures in wet, aqueous or liquid environments; for detection, qualification and/or quantification processes in wet, aqueous or liquid environments; for optical adjustments in wet, aqueous or liquid environments; and/or for in situ detection, qualification and/or quantification processes in liquid probe or sample environments, e.g. in blood, serum, urine, saliva, lymph etc. samples. Corresponding environments may be present or generated, for example, in microfluidic devices, cartridges, reaction chambers or derivatives or subforms thereof, e.g. in devices, cartridges, systems or reactions chambers as described herein.

In a specific embodiment the transformed material, e.g. plastic material, i.e. the material being transformed into an optically modulating state keeps its optical properties in a wet, aqueous or liquid environment, e.g. in solvents. The transformation method works in particular without the necessity of using solvents, e.g. organic solvents, for printing or marking purposes. Furthermore, the transformed material may be persistant to solvents or liquids which are capable of removing superficially applied colors or dyes.

In a further aspect optically modulating material may be produced by a method as defined herein. Optically modulating material may be obtained with, be obtainable by or be produced by a method for the transformation of material, e.g. plastic material, as defined herein.

In one embodiment the optically modulating material, e.g. plastic material, obtained with, obtainable by or produced by a method for the transformation of material, e.g. plastic material, as defined herein comprises a datamatrix of optically modulating elements. A "datamatrix" as used herein may comprise a one or two-dimensional matrix barcode, e.g. consisting of or comprising optically distinguishable fields or modules arranged in different forms, e.g. as squares or rectangular pattern. The information to be encoded may be any suitable information, e.g. text, raw data, images, pictograms etc. For example, information on a device type, manufacturing date, manufacturing lot, spatial properties of the apparatus, component, device, cartridge etc. or sub-elements thereof, encountered peculiarities during quality checks, the amount, size, position etc. of comprised elements or components etc. may be encoded. Furthermore, encoded information may relate to physiochemical properties of an apparatus, component, device, cartridge etc. Such properties include, for example, analytes for which devices or test zones are configured to assay. Other properties include the identity and properties of reagents stored in the device and date information (e.g., the expiration date) of the device.

Typically, a data size from a few bytes up to 2 kilobytes or more may be used. The length of the encoded data may be made dependent on the symbol dimension used. In a further embodiment, error correction codes may be added to increase symbol strength.

In some embodiments the optically modulating material, e.g. plastic material, may comprise one or more datamatrixes wherein the datamatrix may be composed of optically modulating spots. In a further embodiment the optically modulating material, e.g. plastic material, may comprise one or more datamatrixes wherein the datamatrix may be composed of optically modulating dots, lines, symbols, fields, circles, squares, geometric forms, or combinations thereof. The spots, lines or other geometric forms may, for example, be positioned in short distance to each other in order to provide the optical effect of squares or rectangular pattern.

In another embodiment the optically modulating material, e.g. plastic material, obtained with, obtainable by or produced by a method for the transformation of material, e.g. plastic material, as defined herein comprises a reference mark. The term "reference mark" as used herein refers to a fiducial mark of any suitable size or shape. An exemplary shape is a cross, a typical character, a drawing or the like. A reference mark may also be in the form of a line, a rectangle, a dot etc. A reference mark may, for example, be detected on the material, e.g. plastic material, during optical recognition processes, focusing processes, alignment processes, positioning processes etc. carried out on the material. A reference mark or fiducial mark, in one embodiment, may be employed for the alignment of arrays of elements, for the alignment of components of such arrays or for determination of the layout of probes on the array. An example of an array is a micro-array.

A "micro-array" as used herein may include a certain material, such as a probe material, which may, for example, have an increased binding affinity for a target material, immobilized to a plurality of distinct regions on a substrate. In the micro-array, the regions may comprise at least one spot, and generally, at least two spots or regions are arranged on the substrate with an interval separating them or without an interval separating them. Exemplary embodiments of the probe material may include a biomaterial, such as deoxyribonucleic acid ("DNA"), ribonucleic acid ("RNA"), complementary DNA ("cDNA"), messenger RNA ("mRNA"), protein, sugar or other similar materials. Exemplary embodiments of the substrate may be formed of glass, silicon, plastic, ceramic, quartz or other materials with similar characteristics.

In a further embodiment a reference mark, e.g. in the form of a line, a rectangle, a dot, or any other marking as described herein, e.g. a figure, symbol, character etc. may be present in or on a material in conjunction with a micro-array as defined above. For example, a micro-array may be accompanied or surrounded by such reference marks or markings. In some embodiments, the micro-array is on the same surface as the reference marks. In another embodiment, the micro-array is on a different surface in comparison to the reference marks. In further embodiments, the micro-array may be mounted in a spatially defined manner with respect to the reference marks. Additionally or alternatively, the micro-array itself may comprise a reference mark or marking as described herein, e.g. comprise regions, geometric elements, symbols, characters etc. composed of optically modulating material as described herein.

In a specific embodiment material, e.g. plastic material, comprising optically modulating reference marks as described herein may thus be used for the production, manufacture or generation of substrates, casings, devices, cartridges, systems or components thereof etc. comprising a micro-array. Correspondingly obtained substrates, casings, devices, cartridges, or systems may, for example, be identified, aligned, positioned, repositioned and/or calibrated based on the presence of the reference mark. The calibration may in specific embodiments be a qualitative calibration, e.g. based on the presence and/or position and/or wavelength of emitted light of a reference mark. The calibration may in specific embodiments be a quantitative calibration, e.g. based on the intensity or size of a reference mark. These processes may be carried out with optical readers or instruments capable of detecting the light emitted from the reference mark. In a specific embodiment, the emitted light may have a wavelength different from the wavelength emitted from markers used on the array, e.g. optical markers used on micro-arrays comprising DNA, RNA, proteins etc.

In some embodiments material, e.g. plastic material, comprising optically modulating elements as described herein may be used as a fluorescence standard for validating and/or calibrating optical readers, systems or instruments capable of detecting the light emitted from the reference mark. In some embodiments, the validation and/or calibration may be performed based on the presence and/or position and/or wavelength and/or intensity and/or size of emitted light of an optically modulating element.

In a further aspect, a method comprises the application of laser radiation to a material for marking the surface of the material, wherein the marked surface is optically modulating. The term "marking the surface" as used herein refers to the generation of spots, areas or other geometrical elements or forms on said surface, which are distinguishable from their surrounding(s). This distinction includes at least an optical excitability of the marked surface, which is not present in the surroundings of the marked surface. "Optical excitability" as used herein refers to an optically modulating state as defined herein. In one embodiment the optical excitability may be similar to a fluorescence, or be a fluorescent like state of the marked surface such as the emission of radiation at a wavelength different from the excitation wavelength as described herein. "Surface" as used herein refers to the outermost layer of material, e.g. plastic material. The surface may be of any roughness or shape and/or may be planar, or comprise crates, grooves or other structural modifications. In some embodiments, the surface may not only encompass the outermost layer of a material, but also a layer underneath, e.g. in materials comprised of various layers, for instance various thin layers.

The laser radiation to be employed in the method for marking the surface of a material comprises in some embodiments the application of an amount of energy of about 0.05 nJoule/$\mu m^2$ to about 150 $\mu$Joule/$\mu m^2$ treated surface or per single element/spot. In a further embodiment the amount of energy may be between about 0.05 nJoule/$\mu m^2$ to about 100 $\mu$Joule/$\mu m^2$ treated surface or per single element/spot, e.g. in a range of about 0.5 nJoule/$\mu m^2$ to about 50 $\mu$Joule/$\mu m^2$, a range of about 10 nJoule/$\mu m^2$ to about 25 $\mu$Joule/$\mu m^2$, a range of about 0.1 nJoule/$\mu m^2$ to about 20 nJoule/$\mu m^2$, a range of about 0.1 nJoule/$\mu m^2$ to about 10 nJoule/$\mu m^2$ or a range of about 100 nJoule/$\mu m^2$ to 200 nJoule/$\mu m^2$. For example, the energy may be at about 1 nJoule/$\mu m^2$, 5 nJoule/$\mu m^2$, 10 nJoule/$\mu m^2$, 150 nJoule/$\mu m^2$ treated material or per single element/spot.

The amount of energy may be provided in the form of laser radiation pulses. Examples of application times for the pulses are ranges of about 0.05 $\mu$s to 10 ms, 0.1 $\mu$s to 5 ms, 1 $\mu$s to 1 ms, or pulses of 2 $\mu$s, 3 $\mu$s, 4 $\mu$s, 5 $\mu$s, 6 $\mu$s, 7 $\mu$s, 8 $\mu$s, 9 $\mu$s, 10 $\mu$s, 20 $\mu$s, 30 $\mu$s, 50 $\mu$s, 100 $\mu$s, 200 $\mu$s, 300 $\mu$s, 400 $\mu$s, 500 $\mu$s, 600 $\mu$s, 700 $\mu$s, 800 $\mu$s, 900 $\mu$s, 1 ms. The amount of energy to be applied may be adapted to the material used, the surface structure, the surface material, the type of modification envisaged, the laser radiation source used, the laser type used, the laser model used or any other suitable parameter known to the person skilled in the art. The laser types, the wavelength of the laser radiation to be employed and further parameters etc. are described herein above.

In a further embodiment the optical excitation of the marked surface is a broadband light excitation. "Broadband light excitation" as used herein relates to an excitation over a broad range of the visible and near-visible light spectrum, e.g. from about 400 nm to about 700 nm.

In a specific embodiment the optical excitation of the marked surface is an excitation in a wavelength spectrum of about 380 nm to about 540 nm and/or a wavelength spectrum of about 635 nm to about 655 nm For example, the marked surface may absorb light at a wavelength of about 380 nm, 390 nm, 400 nm, 410 nm, 420 nm, 430 nm, 440 nm, 450 nm, 460 nm, 470 nm, 480 nm, 490 nm, 500 nm, 510 nm, 520 nm, 530 nm, 540 nm, and/or 630 nm, 635 nm, 640 nm, 645 nm, 650 nm, 655 nm or 660 nm.

In a specific embodiment the marked surface may emit upon excitation, e.g. upon an excitation as described above, light in a wavelength spectrum of about 550 nm to about 800 nm. For example, the marked surface may emit upon excitation light at a wavelength of about 540 nm, 550 nm, 560 nm, 570 nm, 580 nm, 590 nm, 600 nm, 610 nm, 620 nm, 630 nm, 640 nm, 650 nm, 660 nm, 670 nm, 680 nm, 690 nm, 700 nm, 710 nm, 720 nm, 730 nm, 740 nm, 750 nm, 760 nm, 770 nm, 780 nm, 790 nm, 800 nm, or 810 nm. In one embodiment, the marked surface may emit upon excitation light at a wavelength of about 593 nm. In a further embodiment, the marked surface may emit upon excitation light at a wavelength of about 685 nm. In a further embodiment, the marked surface may emit upon excitation light at a wavelength spectrum of about 560 nm to about 660. In a further embodiment, the marked surface may emit upon excitation light at a wavelength spectrum of about 660 nm to about 700 nm. The marked surface may further emit upon excitation light at more than one wavelength, e.g. at two or more of the above indicated wavelengths. In a further embodiment, the marked surface may upon excitation at a wavelength of about 510 nm to about 530 nm emit light at a wavelength of about 560 to 600 nm and/or 660 to 700 nm.

In some embodiments the marked surface may emit upon excitation light at peak wavelengths of 593 nm and/or 685 nm.

In another embodiment a method comprises the production of an apparatus, device, microfluidic device, cartridge, reaction chamber, object or utility or instrument, wherein said production comprises the employment of optically modulating material as component for said apparatus, device, microfluidic device, cartridge, reaction chamber, object of utility or instrument as described herein. In a specific embodiment a method comprises the production of an optical instrument such as a lense, eyeglasses, sunglasses, a contact lense, a camera, an optical detection apparatuses etc. or components thereof, wherein optically modulating material as described herein is used as starting material, intermediate material or as component of the instruments. In a further specific embodiment, a method comprises the production of an object of utility, e.g. a straw, tableware, a can, a box, a bottle.

In a further specific embodiment a method for the production of an apparatus, device, microfluidic device, cartridge, reaction chamber or instrument comprises one or more steps wherein the material, e.g. plastic material, of the apparatus, device, microfluidic device, cartridge, reaction chamber, object of utility or instrument or of one or more components thereof is transformed into an optically modulating state as defined herein.

For example, apparatuses, devices, microfluidic devices, cartridges, reaction chambers, objects of utility or instruments, e.g. optical instruments such as lenses, eyeglasses, sunglasses, contact lenses, cameras, optical detection apparatuses or components thereof, or objects of utility, e.g. a straw, tableware, a can, a box, a bottle, which comprise optically modulating elements, e.g. geometrical elements, characters, figures, codes, datamatrixes, or three dimensional forms such as holograms or reliefs, may accordingly be provided.

In a further aspect material comprising a marked surface, wherein said marked surface is optically modulating, may be produced by a method for marking the surface of a material as defined herein. Material may be obtained with, obtainable by or produced by a method for marking the surface of a material as described herein.

In one embodiment, the material comprising a marked surface may be a plastic material. The material may also be of a combination of a non-plastic material and a plastic material, e.g. a composite material comprising a plastic surface and one or more a non-plastic layers. Such non-plastic components may be metals, biological compounds such as proteins, peptides, nucleic acids, or derivatives thereof, silica, glass etc. Furthermore, the plastic material may comprise non-plastic additives as described herein.

In a further embodiment, the plastic material may be a thermoplastic or elastomeric material as described herein above.

In another embodiment, the plastic material may be an organic polymer selected from the group consisting of polyethylene, polypropylene, polystyrene, polycarbonate and polycycloolefin as described above.

In a further aspect material may comprise or be covered or at least partially be covered by a surface comprising one or more laser marks, wherein said laser mark is optically modulating. Material may thus comprise or be covered or be at least partially covered by a surface comprising one or more laser marks, wherein said laser mark is optically modulating. The term "one or more" as used herein refers to at least one laser mark, 2 laser marks, 3, 4, 5, 6, 7, 8, 9, 10, 20, 30, 40, 50, 60, 70, 80, 90, 100, 200, 300, 500, 1000, 2000, 3000, 5000, 7500 or more laser marks per single surface of a material. Also envisaged is every natural number of laser marks between the above indicated numbers. The number may vary in dependence of the size of the surface. For instance, one laser mark may be present per 10 $mm^2$ of surface. The term "laser mark" as used herein refers to a spot, area or other shape or form on the surface of a material, which is obtained by the application of laser radiation. A mark may be a single element or a conjunction or array of single marks. A laser mark is typically distinguishable from the surrounding surface. It may, for example, comprise a region or point of ablation, a crate in a planar or quasi planar surface, a scratch in a planar or quasi planar surface, a hole in a planar or quasi planar surface, an embossment in a planar or quasi planar surface, a rim of material in a planar or quasi planar surface, or a planar or quasiplanar region or point in a differently structured surface, e.g. in a rough surface, or in a surface comprising protrusions or protuberances. A laser mark as described herein is optically modulating as defined herein above.

In one embodiment the laser mark on the surface of a material is obtained from the application of laser radiation of an energy of about 0.05 nJoule/$\mu m^2$ to about 150 µJoule/$\mu m^2$ treated surface. In a further embodiment the amount of energy may be between about 0.05 nJoule/$\mu m^2$ to about 100 $\mu$Joule/$\mu m^2$ treated surface or per single element/spot, e.g. in a range of about 0.5 nJoule/$\mu m^2$ to about 50 $\mu$Joule/$\mu m^2$, a range of about 10 nJoule/$\mu m^2$ to about 25 $\mu$Joule/$\mu m^2$, a range of about 0.1 nJoule/$\mu m^2$ to about 20 nJoule/$\mu m^2$, a range of about 0.1 nJoule/$\mu m^2$ to about 10 nJoule/$\mu m^2$ or a range of about 100 nJoule/$\mu m^2$ to 200 nJoule/$\mu m^2$. For example, the energy may be at about 1 nJoule/$\mu m^2$, 5 nJoule/$\mu m^2$, 10 nJoule/$\mu m^2$, 150 nJoule/$\mu m^2$ treated material or per single element/spot. The amount of energy to be applied may be adapted to the surface form, structure or the material of the surface, the type of modification envisaged, the laser radiation source used, the laser type used, the laser model used or any other suitable parameter known to the person skilled in the art.

In some embodiments, the laser mark may emit upon excitation, e.g. upon an excitation as described above or below, light in a wavelength spectrum of about 550 nm to about 800 nm. For example, the laser mark may emit upon excitation light at a wavelength of about 540 nm, 550 nm, 560 nm, 570 nm, 580 nm, 590 nm, 600 nm, 610 nm, 620 nm, 630 nm, 640 nm, 650 nm, 660 nm, 670 nm, 680 nm, 690 nm, 700 nm, 710 nm, 720 nm, 730 nm, 740 nm, 750 nm, 760 nm, 770 nm, 780 nm, 790 nm, 800 nm, or 810 nm. In one embodiment, the laser mark may emit upon excitation light at a wavelength of about 593 nm. In a further embodiment, the laser mark may emit upon excitation light at a wavelength of about 685 nm. In a further embodiment, the laser mark may emit upon excitation light at a wavelength spectrum of about 560 nm to about 660. In a further embodiment, the laser mark may emit upon excitation light at a wavelength spectrum of about 660 nm to about 700 nm. The laser mark may further emit upon excitation light at more than one wavelength, e.g. at two or more of the above indicated wavelengths. In a further embodiment, the laser mark may upon excitation at a wavelength of about 510 nm to about 530 nm emit light at a wavelength of about 560 to 600 nm and/or 660 to 700 nm.

In one embodiment the laser mark may emit upon excitation light at peak wavelengths of 593 nm and/or 685 nm.

In a further embodiment the optical excitation of the laser mark is a broadband light excitation as described herein above.

In a specific embodiment the optical excitation of the laser mark is an excitation in a wavelength spectrum of about 380 nm to about 540 nm and/or a wavelength spectrum of about 635 nm to about 655 nm. For example, the laser mark may absorb light at a wavelength of about 380 nm, 390 nm, 400 nm, 410 nm, 420 nm, 430 nm, 440 nm, 450 nm, 460 nm, 470 nm, 480 nm, 490 nm, 500 nm, 510 nm, 520 nm, 530 nm, 540 nm, and/or 630 nm, 635 nm, 640 nm, 645 nm, 650 nm, 655 nm or 660 nm.

In a specific embodiment the material comprising a surface comprising one or more laser marks is a plastic material. The material may also be of a combination of a non-plastic material and a plastic material, e.g. a composite material comprising a plastic surface and one or more a non-plastic layers. Such non-plastic components may be metals, biological compounds such as proteins, peptides, nucleic acids, or derivatives thereof; silica, glass etc. Furthermore, the plastic material may comprise non-plastic additives as described herein.

In a further embodiment the plastic material may be a thermoplastic or elastomeric material as described herein above.

In another embodiment the plastic material may be an organic polymer selected from the group consisting of polyethylene, polypropylene, polystyrene, polycarbonate and polycycloolefin as described herein above.

In another aspect a datamatrix on a material may be composed of or comprise a laser mark, wherein said laser mark is optically modulating. A datamatrix may be datamatrix as defined above, e.g. comprising a one or two-dimensional matrix barcode consisting of optically distinguishable fields or modules arranged in different forms, e.g. as squares or rectangular pattern. The information to be encoded may be any suitable information, e.g. text, raw data, images, pictograms etc. For example, information on a device type, manufacturing date, manufacturing lot, spatial properties of the apparatus, component, device, cartridge etc. or sub-elements thereof, encountered peculiarities during quality checks, the amount, size, position etc. of comprised elements or components etc. may be encoded. Furthermore, encoded information may relate to physiochemical properties of an apparatus, component, device, cartridge etc. Such properties include, for example, analytes for which devices or test zones are configured to assay. Other properties include the identity and properties of reagents stored in the device and date information (e.g., the expiration date) of the device. In some embodiments the material on which the datamatrix is located can be a plastic material, e.g. a plastic material as defined herein above. In further embodiments, material may also include an apparatus, a device, a cartridge, a reaction chamber, a microfluidic device, or reaction zone being present in such entities, or any component thereof or any combination thereof.

In one embodiment the laser mark of the datamatrix may emit upon excitation, e.g. upon an excitation as described herein, light in a wavelength spectrum of about 550 nm to about 800 nm as described herein above.

In another embodiment, the laser mark of the datamatrix may emit upon excitation light at peak wavelengths of 593 nm and/or 685 nm as described herein above.

In a further embodiment, the optical excitation of the laser mark of the datamatrix may be a broadband light excitation as described herein above.

In a specific embodiment, the optical excitation of the laser mark of the datamatrix may be an excitation in a wavelength spectrum of about 380 nm to about 540 nm and/or a wavelength spectrum of about 635 nm to about 655 nm as described herein above.

In some embodiments, the datamatrix may be composed of optically modulating laser marks, which form, comprise or are geometric forms, geometric pattern, spots, dots, lines, squares, circles, characters, symbols, drawings, barcode or any combination thereof.

In some embodiments, conjunctions of datamatrixes on a material as defined above are also envisaged, e.g. datamatrixes encoding different types of information being located in different sections of a device or apparatus, or in different reaction zones of such entities.

In another aspect, a reference mark on a material may be composed of or comprise a laser mark, wherein said laser mark is optically modulating. A reference mark may be reference mark as defined above, e.g. a fiducial mark of any suitable size or shape, such as a cross, a character, a drawing or the like. A reference mark may also be in the form of a line, a rectangle, a dot etc. A reference mark may, for example, be detected on the material, e.g. plastic material, during optical recognition processes, focusing processes, alignment processes, positioning processes etc. carried out on the material.

In some embodiments, the material on which the reference mark is located can be a plastic material, e.g. a plastic material as defined herein above. In further embodiments, the material on which the reference mark is located may also include an apparatus, a device, a cartridge, a reaction chamber, a microfluidic device, or reaction zone being present in such entities, or any component thereof or any combination thereof.

In one embodiment the laser mark of the reference mark may emit upon excitation, e.g. upon an excitation as described herein, light in a wavelength spectrum of about 550 nm to about 800 nm as described herein above.

In another embodiment, the laser mark of the reference mark may emit upon excitation light at peak wavelengths of 593 nm and/or 685 nm as described herein above.

In a further embodiment, the optical excitation of the laser mark of the reference mark may be a broadband light excitation as described herein above.

In a specific embodiment, the optical excitation of the laser mark of the reference mark may be an excitation in a wavelength spectrum of about 380 nm to about 540 nm and/or a wavelength spectrum of about 635 nm to about 655 nm as described herein above.

In a specific embodiment, the reference mark on a material may be an alignment mark. The term "alignment mark" as used herein refers to a mark suitable for identifying a target position or region or sector in a material, e.g. a device, cartridge, casing, reaction chamber etc., and/or for allowing focusing procedure on said marking, and/or for allowing a positing or repositioning action of an interacting device or apparatus or reader or components thereof with the entity comprising the alignment mark. Such a positioning or repositioning action may, for example, comprise the decrease or increase of angles or inclinations between an alignment mark and interacting device or apparatus or reader or components thereof. Alignment marks also can include physical structures like microstructures and the like. In a further specific embodiment the reference mark on a material may be an array alignment mark. The term "array alignment mark" refers to a mark suitable for identifying a target position or region or sector in on a reaction chamber, cartridge, or casing comprising an array, e.g. an micro-array as described above, or on the array itself or the underlying substrate or material; and/or suitable for allowing a focusing procedure on said marking; and/or suitable for allowing a positioning or repositioning action of an interacting device or apparatus or reader or components thereof with the entity comprising the alignment mark. Such a positioning or repositioning action may, for example, comprise the decrease or increase of angles or inclinations between the array alignment mark and the interacting device or apparatus or reader or components thereof. The action may, for example be carried out by optical readers or instruments capable of detecting the light emitted from the reference mark. In a specific embodiment, the emitted light may have a wavelength different from the wavelength emitted from markers used on the array, e.g. optical markers used on micro-arrays comprising DNA, RNA, proteins etc.

In another aspect material as described herein above, e.g. optically modulating material, or material comprising a laser mark or marking or a marked surface, wherein said mark or marking or marked surface is optically modulating may be used for the manufacture or production of an apparatus, device, microfluidic device, cartridge, reaction chamber, object of utility or instrument, or may be used as component for the manufacture or production of an apparatus, device, microfluidic device, cartridge, reaction chamber, object of utility or instrument. Manufacture or production details and/or processes are known to the person skilled in the art. Examples of devices, apparatuses, microfluidic devices etc., which may be manufactured with the material as defined herein, as well as processes for the their production or manufacture can be derived from Fundamentals and Applications of Microfluidics, Nam-Trung Nguyen, Steve Wereley, 2002, Artech House Publishers; $1^{st}$ ed; or in Microsystem Engineering of Lab-on-a-Chip Devices, Oliver Gerike et al., 2008, Wiley-VCH; $2^{nd}$ edition, which are incorporated by reference in their entirety. Examples of instruments for whose manufacture material as described herein may be used comprise optical instruments such as lenses, eyeglasses, sunglasses, contact lenses, cameras, optical detection apparatusses or components thereof etc. Examples of objects of utility for whose manufacture material as described herein may be used comprise a straw, tableware, a can, a box or a bottle or components thereof etc.

Correspondingly obtained apparatuses, devices, microfluidic devices, cartridges, objects of utility or instruments may comprise optically modulating spot elements, reference marks, geometric forms, marked surfaces, two or three dimensional forms etc. as described herein.

In another aspect a method for the manufacture or production of an apparatus, device, microfluidic device, cartridge, reaction chamber or components thereof, comprises the step of transforming material or a part of the material of said apparatus, device, microfluidic device, cartridge, reaction chamber into an optically modulating state the application of laser radiation to the material. The transformation of material includes in one embodiment the application of laser radiation as define herein above. In another embodiment the transformed material is present in an optically modulating state, as defined herein above.

In a specific embodiment the material to be transformed is plastic material as defined herein above, e.g. thermoplastic material or elastomeric material as described herein. The material may also be a combination of plastic material with other materials, e.g. metals, silica etc. as described herein. Processes for the manufacture of a device besides the indicated transformation steps are known to the person skilled in the art and can, for example, be derived from Fundamentals and Applications of Microfluidics, Nam-Trung Nguyen, Steve Wereley, 2002, Artech House Publishers; $1^{st}$ ed; or in Microsystem Engineering of Lab-on-a-Chip Devices, Oliver Gerike et al., 2008, Wiley-VCH; $2^{nd}$ edition, which are incorporated by reference in their entirety.

In another aspect the device obtained by the method of manufacture, or when using material as described herein, is a device comprising a first channel having an inlet opening, and a longitudinal section in fluid communication with the inlet opening. Material transformed into an optically modulating state may, for example, be used for the production or be present in the first channel, in or near the inlet opening, and/or at the longitudinal section in fluid communication with the inlet opening.

In one embodiment the device obtained by the method of manufacture, or when using material as described herein, is a device comprising a first channel having an inlet opening, an outlet and a longitudinal section between said inlet and said outlet. Material transformed into an optically modulating state may, for example, be used for the production or be present in the first channel, in or near the inlet opening, in or near the outlet opening, and/or at the longitudinal section between the inlet or outlet. Further forms of the device or cartridge are also envisaged, e.g. devices wherein only an inlet port is present, i.e. self-contained devices or cartridges.

In one embodiment the device obtained by the method of manufacture, or when using material as described herein, is a device which comprises a first channel having an inlet opening, an outlet, and a longitudinal section between said inlet opening and said outlet, a channel including a capillary inlet; and a detection region in fluid communication with the capillary inlet. Material transformed into an optically modulating state may, for example, be used for the production or be present in the capillary inlet and/or the detection region, in or near the channel including the inlet or outlet. Further forms of the device or cartridge are also envisaged, e.g. devices wherein only an inlet port is present, i.e. self-contained devices or cartridges.

In one embodiment the device obtained by the method of manufacture, or when using material as described herein, is a device which comprises a first channel having an inlet opening, an outlet, and a longitudinal section between said inlet opening and said outlet, a channel including a capillary inlet; and a detection region in fluid communication with the capillary inlet; and a microfluidic flow path having an at least partially deformable wall and being in fluid communication with the detection region of the channel. Material transformed into an optically modulating state may, for example, be used for the production or be present in the capillary inlet and/or the detection region, in or near the microfluidic flow path, in or near the channel including the inlet or outlet, and/or at the deformable wall section. Further forms of the device or cartridge are also envisaged, e.g. devices wherein only an inlet port is present, i.e. self-contained devices or cartridges. Examples of such devices and further details are described in International Patent Application WO 2008/135564 or WO 2009/112594 (which are incorporated by reference in their entirety).

In another embodiment the device obtained by the method of manufacture, or when using material as described herein, is a device for qualitatively and/or quantitatively detecting molecular interactions between probe molecules and target molecules, comprising a micro-array comprising probe molecules immobilized in array elements, said micro-array being disposed on a first surface of the device; and a reaction chamber formed between the first surface including the micro-array disposed thereon, and a second surface. Material transformed into an optically modulating state may, for example, be used for the production or be present in the first surface of the device, the reaction chamber formed between the first surface including the micro-array disposed thereon, and/or the second surface. Further forms or derivatives of the device are also envisaged, e.g. devices wherein the micro-array may be disposed on the second surface. Examples of such devices and further details are described in International Patent Application WO 2005/108604 (which is incorporated by reference in its entirety).

In another embodiment the device obtained by the method of manufacture, or when using material as described herein, is a device which comprises first and second substrates defining a channel therebetween, at least one of the substrates being flexible, the channel comprising an array of spaced-apart test zones, each test zone comprising a probe compound configured to participate in an assay for a target analyte. Material transformed into an optically modulating state may, for example, be used for the production or be present in the channel between the first and second substrates, and/or on or in proximity to the test zones. Further forms or derivatives of the device are also envisaged. Examples of such devices and further details are described in International Patent Application WO 2008/062048 (which is incorporated by reference in its entirety).

In another embodiment the device obtained by the method of manufacture, or when using material as described herein, is a device which comprises a reaction chamber formed within a chamber body between a first surface and a second surface. Material transformed into an optically modulating state may, for example, be used for the production or be present in the first surface and/or second surface. Further forms or derivatives of the device are also envisaged, e.g. devices wherein the first surface comprises a micro-array and/or wherein the distance between the micro-array and the second surface is variable. In another embodiment the device obtained by the method of manufacture, or when using material as described herein, is a device which comprises a reaction chamber formed within a chamber body between a first surface and a second surface, wherein the second surface is located opposite to the first surface, wherein the distance between the first surface and the second surface is variable at least in one or more parts of the surface area of the first surface and/or the second surface. Material transformed into an optically modulating state may, for example, be used for the production or be present in the first surface and/or second surface. Further forms or derivatives of the device are also envisaged, e.g. devices wherein the first surface comprises a micro-array and/or wherein the distance between the micro-array and the second surface is variable.

In another embodiment the device obtained by the method of manufacture, or when using material as described herein, is a device which comprises a reaction chamber formed within a chamber body between a first surface and a second surface, wherein the second surface is located opposite to the first surface; and one or more displacers, wherein the distance between the first surface and the second surface is variable via the one or more displacers at least in one or more parts of the surface area of the first surface and/or the second surface. Material transformed into an optically modulating state may, for example, be used for the production or be present in the first surface and/or second surface and/or in or on the displacer. Further forms or derivatives of the device are also envisaged, e.g. devices wherein the first surface comprises a micro-array and/or wherein the distance between the micro-array and the second surface is variable and wherein the second surface has a displacement structure and/or wherein the displacer or displacement structure is not part of the device, but provided by an external entity. Examples of such devices and further details are described in International Patent Application WO 2007/051863 (which is incorporated by reference in its entirety).

In further embodiments the device obtained by the method of manufacture, or when using material as described herein, is a device or derivative thereof as described, for example, in International Patent Application WO 2008/055915 or WO 2009/013321, which are incorporated by reference in their entirety.

In another embodiment the device obtained by the method of manufacture, or when using material as described herein, is a device comprising a first channel having an inlet opening, and a longitudinal section in fluid communication with the inlet opening; and a control element. In yet another embodiment the device obtained by the method of manufacture, or when using material as described herein, is a device comprising a first channel having an inlet opening, an outlet and a longitudinal section between said inlet and said outlet; and a control element. In another embodiment the device obtained by the method of manufacture, or when using material as described herein, is a device which comprises a cartridge having a microfluidic channel including a capillary inlet; and a detection region in fluid communication with the capillary inlet; a microfluidic flow path having an at least partially deformable wall and in fluid communication with the detection region of the channel; and a control element. Material transformed into an optically modulating state may, for example, be used for the production or be present in the microfluidic channel, the capillary inlet, and/or the detection region, the microfluidic path, in the vicinity of the partially deformable wall and/or be present in or constitute a control element.

The term "control element" as used herein relates to a unit or factor or means which allows the testing, reviewing, examining, scanning, revising or inspecting of the device or sub-unit of the device or system or of a test result or a result of the analysis and also to the possibility to compare, verify and contrast obtained results during and/or after the use of a device or system or during and/or after performing the methods described herein. The term also denotes the performance of such controlling activities. Further forms or derivatives of the devices are also envisaged, e.g. devices additionally comprising a cap comprising a sealing member configured to seal with the inlet and form a fluid circuit including the inlet, the microfluidic channel and the microfluidic flow path. Examples of such devices and further details are described in International Patent Application WO 2008/135564.

In another aspect, material as described herein above, e.g. optically modulating material, or material comprising a laser mark or marking or a marked surface wherein said mark or marking or marked surface is optically modulating may be used for controlling optical parameters. The term "optical parameters" refers to a parameter such as focus, area of an image, exposure time, distance between elements, turbidity etc. These parameters may be linked to the optical excitability of the material. For example, the optical modulation as defined herein of the material may be determined by taking images of the material. Differences of the optical modulation over time, differences of the optical modulation due to changes in intermediate spaces (e.g. in a reaction chamber, device or cartridge, for instance if biological material such as cells is introduced, biological material grows or dies etc.), differences of the optical modulation due to differences in the filling status of a microfluidic channel a, differences of the optical modulation due to changes in the distance between the source and the imaging taking unit etc. may be determined. "Controlling" as used comprises one or more measurement steps for one or more of these parameters and a subsequent comparison with internal or external data, or with data obtained in subsequent or previous measurement steps.

In a specific embodiment the optical parameter which is to be controlled is the focus of an optical device or reading system. In another embodiment a method comprises the checking or controlling of the focus of a detection unit of a system or associated with a device via said optical parameter.

In some embodiments the focus of a detection unit of a system or associated with a device, wherein said system or device comprises or is composed of optically modulating material as described herein, e.g. present or located within a device, system, cartridge or microfluidic channel, may be checked and adjusted if necessary; comprising the steps of adjusting the exposure time for the detection unit; optically detecting an optically modulating element, spot, form etc. in a predefined area of the device, system, cartridge or microfluidic channel; determining a first value indicative for number of optically modulating elements, spot, form etc. in said area; and determining a second value indicative for the usability of the device or system and/or of any procedure, function or method carried out with or in said device or system, based on a comparison of the first value with a threshold value.

The checking of the focus of a detection unit is typically a comparison of one or more parameters with suitable threshold or predefined values. Such parameters are the conversion of light from object points. Such a conversion may, for instance, be determined by circle of confusion criteria as known to the person skilled in the art. An object or image point may accordingly be considered as being in focus if light is converged almost as much as possible based on circle of confusion criteria. If, in a specific embodiment, these criteria are not met, the focus may be adjusted. This may be done automatically, e.g. with the help of electronic or mechanical devices, typically in the form of autofocussing on an object. Suitable techniques, devices, or calculation methods etc. are known to the person skilled in the art. Alternatively, the focus may be adjusted manually. A detection unit may be comprised in a system, e.g. a system for performing assays such as biological, medical, chemical, biochemical assays, cell counting etc. or may be associated with a device wherein assays may be performed such as biological medical, chemical, biochemical assays, cell counting etc. In one embodiment the detection unit may be comprised in a system or device as mentioned herein. In another embodiment the detection unit may be associated with a device as mentioned herein.

The exposure time for the detection unit may be adjusted according to the amount and intensity of light reaching the detection unit, e.g. in reaction to the depth of image field, the distance range over which objects are acceptably sharp or in focus or any other suitable parameter known to the person skilled in the art. The adjustment may be carried out automatically, e.g. with the help of electronic or mechanical devices, typically in the form of an automated comparison to a lookup table. Suitable techniques, devices, lookup tables for threshold values etc. are known to the person skilled in the art. Alternatively, the exposure time may be adjusted manually.

In some embodiments, a value indicative for the number of optically modulating elements, spots, forms etc. may be compared to a threshold value or lookup table. If, for example, the indicative number of such optically modulating elements, spots, forms etc. is zero, i.e. no optically modulating element, spot, form is detectable, the device or system and/or any procedure, function or method carried out with or in said device or system may be considered as non-usable. Alternatively, if, for example, the value indicative for the number of optically modulating elements, spots, forms is much larger than a predefined value or the threshold value, e.g. larger than 100,000, i.e. too many optically modulating elements, spots, forms are detectable, the device or system and/or any procedure, function or method carried out with or in said device system may also be considered as non-usable. Otherwise, i.e. if the value is within a threshold range, e.g. as indicated above, the device or system and/or any procedure, function or method carried out with or in said device system may also be considered as usable and/or be confirmed.

If a non-usability situation is encountered in this context the usage of the device or system may be discontinued and/or any results obtained may be disregarded. Corresponding information may be recorded electronically or encoded in a barcode or any other suitable coding material. Such a barcode may, for instance, be attached to a device or microfluidic channel.

Additionally or alternatively, encountering a non-usability situation may lead to one or more adjustment reactions. The adjustment reactions may be determined in reaction to the value indicative for the number of optically modulating, elements, spots, forms. If, for example, no optically modulating, elements, spots, forms are detected, the focus of the detection system may be adjusted or further adjusted if it was already adjusted before. In some embodiments, the adjustment may be accomplished by a variation of the distance between the detection system and a material comprising said optically modulating, elements, spots or forms, e.g. a microfluidic channel, e.g. by using increments of 0.01, 0.05, 0.5, 0.75, 0.8, 0.9, 1.0, 1.1, 1.2, 1.5, 2, 3, 4, 5, 10, 20, 50 or 100 μm or any other suitable increment which may depend on the nature, size and form of the detection unit used. Such a modification may be reiterated one or several times, followed or preceded by the other method steps as described herein. Furthermore, the exposure time may be adjusted or further adjusted if it was already adjusted before. The exposure time may, for example, be increased or decreased by about 10, 20, 30, 50, 100, 200, 500, 1000 or 10.000%. Such a modification may be reiterated one or several times, followed or preceded by the other method steps as described herein.

A reiteration of additional adjustments of the focus, predefined area and/or exposure time may be carried out for each of the parameters of focus, predefined area and exposure time independently or for a combination of parameters. Such a reiteration may be carried out for 1 to about 20 times, e.g. 2, 3, 4, 5, 6, 7, 8, 9, 10 times.

If, after a reiteration of additional adjustments, a non-usability situation prevails the usage of the device or system may be discontinued and/or any results obtained may be disregarded.

If, on the other hand, a comparison of a value indicative for the usability of the device or system is within a predefined range the device or system may be continued to be used and/or the results obtained or to be obtained with said device or system may be confirmed.

The methods may accordingly be carried out before or after carrying out an assay as described herein. Alternatively, the method may be carried out during the performance of an assay as described herein.

In further embodiments the steps of the method mentioned above may be carried out in a different order, e.g. first a value indicative for the number of optically modulating elements, spots, forms etc. in an area may be determined, subsequently a value indicative for the usability may be determined. If at this stage a non-usability situation is encountered the focus may be checked and/or adjusted and/or the exposure time may be adjusted and/or the area of optical detection may be adjusted as described herein.

In specific embodiments, the threshold value for controlling the focus position may be for instance the detection of minimum number of 3 optically modulating elements, spots or forms as lower limit and about 10,000 optically modulating elements, spots or forms as upper limit, for instance 5, 10, 50, 100 or 500 optically modulating elements, spots or forms. If, in a specific embodiment, the second value indicative for the usability of the device or system and/or of any procedure, function or method carried out with or in the device or system is a deviation of not more than 40%, 35%, 30%, 25%, 20%, 15%, 12%, 11%, 10%, 9%, 8%, 7%, 6%, 5%, 4%, 3%, 2% or 1% between the first value, i.e. the value indicative of the number of optically modulating elements, spots or forms etc. in a predefined area of the device, cartridge or microfluidic channel and the threshold value of 3 optically modulating elements, spots or forms or about 10,000 optically modulating elements, spots or forms, the test may be considered as being usable and/or any procedure, function or method carried out with or in the device or system may be confirmed. If a concomitant assay is carried out, corresponding images may be taken and/or recorded and/or further processed.

If, in a further specific embodiment, the second value indicative for the usability of the device or system and/or of any procedure, function or method carried out with or in the device or system is a deviation of more than about 40%, 35%, 30%, 25%, 20%, 15%, 12%, 11%, 10%, 9%, 8%, 7%, 6%, 5%, 4%, 3%, 2% or 1% between the first value, i.e. the value indicative of the number of optically modulating elements, spots or forms in a predefined area of the device, cartridge or microfluidic channel and the threshold value of 3 optically modulating elements, spots or forms, or about 10,000 optically modulating elements, spots or forms, the test may be regarded as being non-usable. In some embodiments, the device or system may be regarded as non-usable and/or any procedure, function, test or method carried out with or in the device or system may be considered as inaccurate. The test or usage of the device or system may accordingly be discontinued and/or the results obtained may be disregarded.

In another aspect, a microfluidic device comprises a first channel having an inlet opening, and a longitudinal section in fluid communication with the inlet opening, wherein said device is at least partially composed of or comprises material which comprises material transformed into an optically modulating state, e.g. plastic material transformed into an optically modulating state. The term "material transformed into an optically modulating state" refers to material as described herein above, e.g. material comprising a laser mark or marking or a marked surface wherein said mark or marking or marked surface is optically modulating or material obtained or obtainable with a method of transformation as defined herein above.

In one embodiment a microfluidic device comprises a first channel having an inlet opening, an outlet and a longitudinal section between said inlet and said outlet wherein said device is at least partially composed of or comprises material which comprises material transformed into an optically modulating state, e.g. plastic material transformed into an optically modulating state. The term "material transformed into an optically modulating state" refers to material as described herein above, e.g. material comprising a laser mark or marking or a marked surface wherein said mark or marking or marked surface is optically modulating or material obtained or obtainable with a method of transformation as defined herein above. Further forms of the microfluidic device are also envisaged, e.g. a microfluidic device wherein only an inlet port is present, i.e. a self-contained device.

In another embodiment a microfluidic device comprises a first channel having an inlet opening, an outlet, and a longitudinal section between said inlet opening and said outlet, wherein said device is at least partially composed of or comprises material which comprises material transformed into an optically modulating state, e.g. plastic material transformed into an optically modulating state. The term "material transformed into an optically modulating state" refers to material as described herein above, e.g. material comprising a laser mark or marking or a marked surface wherein said mark or marking or marked surface is optically modulating or material obtained or obtainable with a method of transformation as defined herein above. Further forms of the microfluidic device are also envisaged, e.g. a microfluidic device wherein only an inlet port is present, i.e. a self-contained device.

In another aspect, a microfluidic device comprises a channel including a capillary inlet; and a detection region in fluid communication with the capillary inlet; wherein said device is at least partially composed of or comprises material which comprises material transformed into an optically modulating state, e.g. plastic material transformed into an optically modulating state as described herein. In an embodiment the capillary inlet and/or the detection region, and/or the channel including the inlet or outlet, may comprise, partially comprise, be composed or be partially composed of said material. Further forms of the device are also envisaged, e.g. devices wherein only an inlet port is present, i.e. self-contained devices or cartridges.

In another embodiment, a microfluidic device comprises a channel including a capillary inlet; and a detection region in fluid communication with the capillary inlet; and a microfluidic flow path having an at least partially deformable wall and being in fluid communication with the detection region of the channel; wherein said device is at least partially composed of or comprises material which comprises material transformed into an optically modulating state, e.g. plastic material transformed into an optically modulating state as described herein. In an embodiment the capillary inlet and/or the detection region, and/or the microfluidic flow path, and/or the channel including the inlet or outlet, and/or the deformable wall section may comprise, partially comprise, be composed or be partially composed of said material. Further forms of the device are also envisaged, e.g. devices wherein only an inlet port is present, i.e. self-contained devices or cartridges. Examples of such devices and further details are described in International Patent Application WO 2008/135564 or WO 2009/112594.

In another aspect a device, e.g. suitable or envisaged for qualitatively and/or quantitatively detecting molecular interactions between probe molecules and target molecule, may comprise a micro-array comprising probe molecules immobilized in array elements, said micro-array being disposed on a first surface of the device; and a reaction chamber formed between the first surface including the micro-array disposed thereon, and a second surface, wherein said device is at least partially composed of or comprises material, which comprises material transformed into an optically modulating state, e.g. plastic material transformed into an optically modulating state as described herein. In an embodiment the first surface of the device, the reaction chamber formed between the first surface including the micro-array disposed thereon, and/or the second surface may comprise, partially comprise, be composed or be partially composed of said material. Further forms or derivatives of the device are also envisaged, e.g. devices wherein the micro-array may be disposed on the second surface. In a specific embodiment, the distance between micro-array and the second surface of the device may be variable. Examples of such devices and further details are described in International Patent Application WO 2005/108604 (which is incorporated by reference in its entirety).

In another aspect, a cartridge may comprise a microfluidic channel including a capillary inlet and a detection region in fluid communication with the capillary inlet, wherein said cartridge is at least partially composed of or comprises material which comprises material transformed into an optically modulating state, e.g. plastic material transformed into an optically modulating state as described herein. In an embodiment the microfluidic channel, and/or the detection region, and/or the capillary inlet may comprise, partially comprise, be composed or be partially composed of said material. Further forms or derivatives of the cartridge are also envisaged, e.g. cartridges comprising an outlet.

In another aspect, a device may comprise a first and second substrates defining a channel therebetween, at least one of the substrates being flexible, the channel comprising an array of spaced-apart test zones, each test zone comprising a probe compound configured to participate in an assay for a target analyte, wherein said device is at least partially composed of or comprises material which comprises material transformed into an optically modulating state, e.g. plastic material transformed into an optically modulating state as described herein. In an embodiment the channel between the first and second substrates of the device, the reaction chamber formed between the first surface including the micro-array and/or one or more test zones may comprise, partially comprise, be composed or be partially composed of said material. Further forms or derivatives of the device are also envisaged. Examples of such devices and further details are described in International Patent Application WO 2008/062048.

In another aspect, a device, e.g. suitable or envisaged for qualitative and/or quantitative detection of particles, comprises a reaction chamber formed within a chamber body between a first surface and a second surface, wherein said device is at least partially composed of or comprises material which comprises material transformed into an optically modulating state, e.g. plastic material transformed into an optically modulating state as described herein. In an embodiment, the first surface and/or second surface may comprise, partially comprise, be composed or be partially composed of said material. Further forms or derivatives of the device are also envisaged, e.g. devices wherein the first surface comprises a micro-array.

In another embodiment, a device, e.g. suitable or envisaged for qualitative and/or quantitative detection of particles, may comprise a reaction chamber formed within a chamber body between a first surface and a second surface, wherein the second surface is located opposite to the first surface, and a microfluidic flow path having an at least partially deformable wall, being in fluid communication with the reaction chamber, wherein said device is at least partially composed of or comprises material which comprises material transformed into an optically modulating state, e.g. plastic material transformed into an optically modulating state as described herein. In an embodiment, the device may comprise one or more optically modulating elements located on either the first or the second surface of the reaction chamber. In a further embodiment, the device may comprise one or more optically modulating elements on the first and the second surface and/or in the microfluidic flow path. In another embodiment, the first surface and/or second surface may comprise, partially comprise, be composed or be partially composed of said material. Further forms or derivatives of the device are also envisaged, e.g. devices wherein the first surface comprises a micro-array and/or wherein the distance between the micro-array and the second surface is variable. In some embodiments, devices comprising a micro-array on the first surface may further comprise one or more optically modulating elements on the first surface of the reaction chamber. The number of modulating elements may vary in dependence of the size of the device, its purpose, the size and form of the elements or other factors. For example, between about 1 to 1000, e.g.

about 10, 20, 30, 40, 50, 60, 70, 80, 90, 100 or more than 100, e.g. about 150, 200, 250, 300, 350, 400, 450, 500, 550, 600, 650, 700, 750, 800, 850, 900, 950, or 1000, or any natural number in between these numbers, or more than 1000 optically modulating elements may be located.

In another embodiment a device, e.g. suitable or envisaged for qualitative and/or quantitative detection of particles, e.g. cells, including, for example, T-helper cells or $CD4^+$ T-cells, may comprise a reaction chamber formed within a chamber body between a first surface and a second surface, wherein the second surface is located opposite to the first surface; and one or more displacers, wherein the distance between the first surface and the second surface is variable via the one or more displacers at least in one or more parts of the surface area of the first surface and/or the second surface, wherein said device is at least partially composed of or comprises material which comprises material transformed into an optically modulating state, e.g. plastic material transformed into an optically modulating state as described herein. In an embodiment, the first surface and/or second surface and/or the displacer may comprise, partially comprise, be composed or be partially composed of said material. Further forms or derivatives of the device are also envisaged, e.g. devices wherein the first surface comprises a micro-array and/or wherein the distance between the micro-array and the second surface is variable and wherein the second surface has a displacement structure and/or wherein the displacer or displacement structure is not part of the device, but provided by an external entity. Examples of such devices and further details are described in International Patent Application WO 2007/051863.

In another aspect a device, e.g. suitable or envisaged for detecting an analyte, may comprise a cartridge having a microfluidic channel including a capillary inlet; and a detection region in fluid communication with the capillary inlet; a microfluidic flow path having an at least partially deformable wall and in fluid communication with the detection region of the channel; and a control element, e.g. as defined herein above, wherein said device is at least partially composed of or comprises material which comprises material transformed into an optically modulating state, e.g. plastic material transformed into an optically modulating state as described herein. In an embodiment, the microfluidic channel, and/or the capillary inlet, and/or the detection region, and/or the microfluidic path, and/or the partially deformable wall and/or the control element may comprise, partially comprise, be composed of or be partially composed of said material. Further forms or derivatives of the device are also envisaged, e.g. devices additionally comprising a cap comprising a sealing member configured to seal with the inlet and form a fluid circuit including the inlet, the microfluidic channel and the microfluidic flow path. Examples of such devices and further details are described in International Patent Application WO 2008/135564.

In another aspect a device, e.g. suitable or envisaged for detecting an analyte, may comprise a cartridge having a microfluidic channel including a capillary inlet; and a detection region in fluid communication with the capillary inlet; a microfluidic flow path having an at least partially deformable wall and in fluid communication with the detection region of the channel; and a cap comprising a sealing member configured to seal with the inlet and form a fluid circuit including the inlet, the microfluidic channel and the microfluidic flow path, wherein said device is at least partially composed of or comprises material which comprises material transformed into an optically modulating state, e.g. plastic material transformed into an optically modulating state as described herein. In an embodiment, the microfluidic channel, and/or the capillary inlet, and/or the detection region, and/or the microfluidic path, and/or the partially deformable wall may comprise, partially comprise, be composed of or be partially composed of said material. Examples of such devices and further details are described in International Patent Application WO 2008/135564.

In another aspect a system, e.g. suitable or envisaged for detecting an analyte, comprises a cartridge having a microfluidic channel including an inlet and a detection region in fluid communication with the inlet; a microfluidic flow path having an at least partially deformable wall and in fluid communication with the detection region of the channel; and a cap comprising a sealing member configured to seal with the inlet and form a fluid circuit including the inlet, the microfluidic channel and the microfluidic flow path; and an optical or fluorescence detector including a light source; a condenser lens; and an objective lens; wherein said system is at least partially composed of or comprises material which comprises material transformed into an optically modulating state, e.g. plastic material transformed into an optically modulating state as described herein. In an embodiment the condenser lens may be a condenser lens obtaining a solid angle of 10° or greater. In a further embodiment the objective lens may be an objective lens obtaining a solid angle of 10° or greater. In yet another embodiment, the microfluidic channel, and/or the inlet, and/or the detection region, and/or the microfluidic path may comprise, partially comprise, be composed of or be partially composed of said material. Further forms or derivatives of the system are also envisaged, e.g. devices which have no optical or fluorescence detector, devices which have a detector for non-fluorescent light, systems without a cap structure. Examples of such systems and further details are described in International Patent Application WO 2010/105802 (which is incorporated by reference in its entirety).

In further embodiments a device or system is a device, system or derivative thereof as described, for example, in International Patent Application WO 2008/055915 or WO 2009/013321, wherein said device or system is at least partially composed of or comprises material which comprises material transformed into an optically modulating state, e.g. plastic material transformed into an optically modulating state as described herein.

In another aspect a device, e.g. suitable or envisaged for detecting an analyte in a sample, comprises a cartridge having a microfluidic channel including a capillary inlet; and a detection region in fluid communication with the capillary inlet; a microfluidic flow path having an at least partially deformable wall and in fluid communication with the detection region of the channel; and a control element, wherein said control element is at least partially composed of or comprises material which comprises material transformed into an optically modulating state, e.g. plastic material transformed into an optically modulating state as described herein. The control element may be a control element as described herein. In one embodiment said control element may be associated with the control of an optical parameter as described herein. In a further embodiment, said control element may be employed in a method of determining the focus as described herein above.

In a further embodiment a device, a system or a cartridge as described herein comprise one or more optically modulating elements. Such elements may, for example, comprise geometrical forms, geometrical pattern, spots, dots, lines, circles, squares, characters, symbols, drawings, barcodes, datamatrixcodes or datamatrixes, or any combination thereof. In a further embodiment said geometrical forms are those described herein above.

In a further embodiment a device, a system or a cartridge as described herein comprise an array of optically modulating spots. Such elements may, for example be present as a geometrically ordered array, or be present in the form of a barcode, character or in any other form or shape. The array may, for example, comprise 2 spots, 3, 4, 5, 6, 7, 8, 9, 10, 20, 30, 40, 50, 60, 70, 80, 90, 100, 200, 300, 500, 1000 or more than thousand spots per unit or surface of the device, system or cartridge.

In a further embodiment said array of optically modulating spots may be in the form of a datamatrix or reference mark, e.g. as described herein above.

In a further embodiment said a device, a system or a cartridge as described herein is at least partially composed of or comprises material as defined herein above, e.g. plastic material, or combinations of plastic material with other material as defined herein above.

In a further aspect a method, e.g. suitable or envisaged for the qualitative and/or quantitative detection of particles, e.g. cells, including, for example, T-helper cells or CD4$^+$ T-cells as mentioned herein above or below, may comprise positioning a sample supposed to comprise one or more species of particles to be detected in a reaction chamber comprised in a device as described herein, e.g. a device at least partially composed of or comprising material which comprises material transformed into an optically modulating state, e.g. plastic material transformed into an optically modulating state as described herein above; displacing at least a part of the sample within the reaction chamber via one or more displacers; and detecting/determining a value indicative for the presence and/or number of one or more species of particles. In an embodiment, the method may additionally comprise an optical control step as described herein above, e.g. the controlling of the checking or adjusting of the focus if necessary. In one embodiment, the method may comprise positioning a sample comprising multiple particles in a reaction chamber, displacing a subset of said multiple particles within the reaction chamber via the one or more displacers, determining one or more values indicative for the number of the subset of particles displaced within the reaction chamber, and optionally calculating the total number of the multiple particles in the reaction chamber from the one or more values obtained during detection. In other embodiments, the method further comprises positioning/introducing one or more agents each comprising one or more detectable moieties into the reaction chamber before performing detection. The one or more agents may be selected from the group consisting of nucleic acids, peptides, protein domains, proteins, carbohydrates, low molecular weight chemical compounds, and analogs and/or mixtures thereof and have binding affinity for one or more particles to be detected. In a further embodiment method may comprise positioning multiple particles of a sample within a detection chamber, displacing some of the multiple particles from the detection chamber so that only a proper subset of the multiple particles remains, optically detecting particles of the subset of multiple particles, and based on the detected particles, determining a value indicative of the number of particles of the subset of particles. In yet another embodiment, the method further comprises determining a value indicative of a number or abundance of particles in the sample based on the value indicative of the number of particles of the proper subset. Optionally, this determination is further based on a size of a detection volume of the detection chamber. In an additional embodiments, the method further comprises repeating a number NR times the steps of positioning multiple particles of the sample within the detection chamber and displacing some of the multiple particles from the detection chamber so that, in each case, only a proper subset of the multiple particles remains, and where NR≥2 and, for a number ND of the NR repetitions, optically detecting particles of the subset of multiple particles and, based on the detected particles, determining a value indicative of the number of particles of the proper subset of particles, where ND≥NR. In another embodiment the method comprises repeating NR times the steps of positioning and displacing comprises, for multiple of the NR repetitions, reintroducing at least some of the displaced multiple particles to the detection chamber. In yet another embodiment, displacing some of the multiple particles may comprise reducing a volume of the detection chamber which, in turn, may comprise reducing a distance between first and second walls of the chamber. In a further embodiment the method may comprise positioning multiple particles of a sample within a detection chamber, displacing some of the multiple particles from the detection chamber so that only a proper subset of the multiple particles remains, optically detecting particles of the subset of multiple particles, and determining the presence of a target particle among the subset of particles. In another embodiment, the method comprises positioning a first multiple of particles of a sample within a detection chamber, reducing a volume of the detection chamber, optically detecting particles within the detection chamber, based on the detected particles, determining a value indicative of the number of particles present within the detection chamber, increasing a volume of the detection chamber, positioning a second multiple of particles of the sample within the detection chamber, reducing a volume of the detection chamber, and based on the detected particles, determining a value indicative of the number of particles present within the detection chamber. Examples of such methods and further details are described in International Patent Application WO 2007/051861 (which is incorporated by reference in its entirety).

In a further aspect a method may comprise labeling particles, e.g. cells, including, for example, T-helper cells or CD4$^+$ T-cells as mentioned herein below, immobilized in the microfluidic channel of a device or system with an optical label or labeling reagent; obtaining a first image comprising at least a subset of the immobilized particles; determining a first value indicative for the number of particles in the first image; obtaining a further image of the subset of immobilized particles after an interim; determining a further value indicative for the number of particles in the further image; determining a third value indicative for the activity and/or quality of the optical label or labeling reagent and/or the quality of an interaction between a particle and a labeling reagent and/or the usability of the device or system and/or of any procedure, function or method carried out with or in said device or system and/or the accuracy of a test result obtained by using said device or system, based on a comparison of the first value and the further value, and using before, between and/or after these steps control elements for focusing and/or aligning said images, wherein said control element is at least partially composed of or comprises material which comprises material transformed into an optically modulating state, e.g. plastic material transformed into an optically modulating state as described herein. In one embodiment the step of obtaining a further image and determining a further value can be repeated at least 2, 3, 5, 10 or n times and the determination of the third value can be based on a comparison of the first and the further value(s). In a further embodiment the third value indicative for the quality of the labeling reagent and/or the quality of an interaction between a particle and a labeling reagent and/or the usability of the device or system and/or of any procedure, function or method carried out with or in said device or system can be an increase of the further value with respect to the first value by at least about 10%, at least about 20% or by at least about 30%. Obtaining such an increase can lead to a continuation of usage of said device or system and/or a confirmation of results obtained with said device or system. In one embodiment, the third value may be compared with a threshold value. Based on this comparison, an action may result. In some embodiments, this action may be one or more of a group comprising displaying an error message, displaying a status message, moving a component relative to another component, performing an algorithm, aborting or continuing an assay, procedure, algorithm etc. Alternatively, an increase of the further value with respect to the first value or a threshold value of more than about less than about 10%, less than about 20% or less than about 30% can indicate the non-usability of the device or system and/or of any procedure or method carried out with or in said device or system. Obtaining such an increase can lead to a discontinuation of usage of said device or system and/or a disregard of results obtained with said device or system.

In a specific embodiment a particle immobilized in the microfluidic channel may be an inorganic substance, a eukaryotic cell, e.g. a mammalian cell, including, for example, a T-helper cell or $CD4^+$ T-cell as mentioned herein below, a bacterium, or a virus. The labeling reagent to be used in the method may be a dye, a ligand or an antibody. Furthermore, the dye, ligand or antibody can be fluorescent or conjugated to a fluorescent element. In a further embodiment the interim between a first and a further image can be between about 10 sec and 30 min, between about 1 min and 15 min, between about 5 min and 10 min, or about 7 min. In a further embodiment, the method comprises: obtaining an image of at least one position of a microfluidic channel comprised in a device or system; introducing a sample into the microfluidic channel; obtaining a further image of the at least one position of a microfluidic channel; analyzing one or more parameters of the images; calculating a value indicative for the presence of a sample in the microfluidic channel and/or the usability of the device or system and/or of any procedure, function or method carried out with or in said device or system, based on the analyzed parameters. In one embodiment the parameter of the image to be used can be a grey value in each image. In one embodiment the value indicative for the presence of a sample in the microfluidic channel and/or the usability of the device or system and/or of any procedure, function or method carried out with or in said device or system can be an increase of the grey value by more than about 50% between the grey value in said image and the grey value in said further image. Obtaining such a value can lead to a continuation of usage of said device or system and/or a confirmation of results obtained with said device or system. Alternatively, an increase of said grey values by less than about 50% between said image and said further image can indicate the non-presence of a sample in the microfluidic channel and/or the non-usability of the device or system and/or of any procedure or method carried out with or in said device or system. Obtaining such an increase can lead to a discontinuation of usage of said device or system and/or a disregard of results obtained with said device or system. In a further embodiment the parameter of the image to be used is the $50^{th}$ to $95^{th}$ percentile or the $90^{th}$ percentile of the grey values in each image. In another embodiment the method may additionally comprises: checking the focus of a detection unit of a system or associated with a device, wherein said system or device comprises one or more optically detectable particles being immobilized within a microfluidic channel, and adjusting the focus if necessary; adjusting the exposure time for the detection unit; optically detecting the one or more particles in a predefined area of the microfluidic channel; determining a first value indicative for the number of particles in said area; and determining a second value indicative for the usability of the device or system and/or of any procedure, function or method carried out with or in said device or system, based on a comparison of the first value with a threshold value; or the method, comprising: placing a lens at a first distance and at a first position with respect to a microfluidic channel of a device or system comprising a liquid sample and one or more optically detectable particles immobilized within a microfluidic channel, taking a first image of at least a subset of said immobilized particles, analyzing at least one parameter of said first image, based on said at least one parameter, placing the lens at a second distance and at the first position with respect to the microfluidic channel, taking a further image of at least a subset of said immobilized particles, determining a first value indicative for the number of particles in said second image, determining a second value indicative for the difference between said first value and a threshold value, and, depending on said second value, taking at the second distance an image of at least a second position of the microfluidic channel or creating an error message, can be performed in combination with a method comprising: labeling particles immobilized in the microfluidic channel of a device or system with an optical label or a labeling reagent; obtaining a first image comprising at least a subset of the immobilized particles; determining a first value indicative for the number of particles in the first image; obtaining a further image of the subset of immobilized particles after an interim; determining a further value indicative for the number of particles in the further image; determining a third value indicative for the activity and/or quality of optical label or the labeling reagent and/or the quality of an interaction between a particle and a labeling reagent and/or the usability of the device or system and/or of any procedure, function or method carried out with or in said device or system, based on a comparison of the first value and the further value, and/or in combination with a method comprising: obtaining an image of at least one position of a microfluidic channel comprised in a device or system; introducing a sample into the microfluidic channel; obtaining a further image of the at least one position of a microfluidic channel; analyzing one or more parameters of the images; calculating a value indicative for the presence of a sample in the microfluidic channel and/or the usability of the device or system and/or of any procedure, function or method carried out with or in said device or system, based on the analyzed parameters. In a further embodiment the method comprises: labeling particles immobilized in the microfluidic channel of a device or system with an optical label or labeling reagent; obtaining a first image comprising at least a subset of the immobilized particles; determining a first value indicative for the number of particles in the first image; obtaining a further image of the subset of immobilized particles after an interim; determining a further value indicative for the number of particles in the further image; determining a third value indicative for the activity and/or quality of the optical label or labeling reagent and/or the quality of an interaction between a particle and a labeling reagent and/or the usability of the device or system and/or of any procedure, function or method carried out with or in said device or system, based on a comparison of the first value and the further value, can be performed in combination with a method comprising: obtaining an image of at least one position of a microfluidic channel comprised in a device or system; introducing a sample into the microfluidic channel; obtaining a further image of the at least one position of a microfluidic channel; analyzing one or more parameters of the images; calculating a value indicative for the presence of a sample in the microfluidic channel and/or the usability of the device or system and/or of any procedure, function or method carried out with or in said device or system, based on the analyzed parameter. In a further embodiment the method can further comprise at least one of the following steps: controlling the presence of a device within or with respect to a detection unit of a system; determining an optical, e.g. fluorescence, background in the microfluidic channel of the device or system; determining a target counting plausibility via the detection of certain target particles in the device or system; controlling the moveability of the device within the detection unit of the system; controlling of accu charge, date plausibility and/or temperature in the device or system; and controlling of software parameters of the system. In a further embodiment, the method comprises: introducing a liquid sample into a microfluidic channel disposed within a microfluidic network, device or system, wherein the microfluidic channel comprises the liquid sample comprising multiple particles, and wherein said microfluidic channel comprises and/or is associated with a control element; forming a mixture comprising at least a portion of the liquid sample and an optical label; forming multiple complexes, each complex comprising one of the multiple particles and at least one of the optical labels; detecting complexes present within a subset of the mixture; performing a control procedure comprising determining a value based on the control element and comparing the value with a predefined value; wherein a matching of both values or a deviation between both values of less than about 30% indicates the usability of the microfluidic channel, device or system and/or of any procedure, function or method carried out with or in said microfluidic channel, device or system, leading to a continuation of usage of said microfluidic channel, device or system and/or a confirmation of results obtained with said microfluidic channel, device or system, and wherein a deviation between both values of more than about 30% indicates the non-usability of the microfluidic channel, the device or system and/or of any procedure or method carried out with or in said microfluidic channel, device or system and/or leads to a discontinuation of usage of said device or system and/or to a disregard of results obtained with said microfluidic channel, device or system. In a further embodiment any of the methods may comprise a step of detecting complexes allowing a detection and/or a diagnosis of a retroviral infection and/or a conclusion on the status of a retroviral infection. The retroviral infection may be an infection with HIV. In some embodiments, a device or system as described herein. In a further embodiment the method comprises: contacting particles immobilized within a microfluidic channel of a microfluidic network, device or system, e.g. cells, including, for example, T-helper cells or $CD4^+$ T-cells as mentioned herein, with an optical label configured to bind the particles; forming complexes, each of the complexes comprising an optical label and a particle immobilized within the microfluidic channel; obtaining a first image comprising at least a subset of the immobilized complexes; determining a first value indicative for the number of complexes in the first image; obtaining a further image of the subset of immobilized complexes after an interim; determining a further value indicative for the number of complexes in the further image; and determining a third value indicative for the activity and/or quality of the labeling reagent and/or the quality of an interaction between a particle and a labeling reagent and/or the usability of the device or system and/or of any procedure, function or method carried out with or in said device or system, based on a comparison of the first value and the further value. The control element may be a control element as described herein. In one embodiment said control element may be associated with the control of an optical parameter as described herein. In a further embodiment, said control element may be employed in a method of determining the focus as described herein above.

In a further aspect a method may comprise providing a device or system comprising material, e.g. plastic material, transformed into an optically modulating state wherein said material comprises a predetermined number of optically modulating elements and/or comprises optically modulating elements of a predetermined size; obtaining an image comprising at least a subset of the elements; determining the number and/or size of the elements comprised in said image; determining a value indicative for the usability of the device or system and/or of any procedure, function or method carried out with or in said device or system and/or the accuracy of a test result obtained by using said device or system, based on a comparison of the determined number and/or size of the elements, with said predetermined number and/or size. In one embodiment the excitable element may be any optically modulating element as described above, e.g. a geometrical form, a geometrical pattern, a spot, dot, line, circle, square, character, symbol, drawing, barcode or datamatrix or datamatrixcode, or any combination thereof.

The term "predetermined number" as used herein refers to a fixed number of such elements, which may be obtained during the modification of a material, e.g. plastic material, as described herein. The number of elements may also be encoded in a datamatrix or barcode being present in or on said device and/or being detectable with the same reader suitable for the determination of the number or size.

The term "predetermined size" as used herein refers to a fixed size of one or more such elements, which may be obtained during the modification of a material, e.g. plastic material, as described herein. Also the size of the elements may be encoded in a datamatrix or barcode being present in or on said device and/or being detectable with the same reader suitable for the determination of the number or size.

In one embodiment a detection unit may be comprised in a system, e.g. a system for performing assays such as biological, medical, chemical, biochemical assays, cell counting etc. or may be associated with a device wherein assays may be performed such as biological medical, chemical, biochemical assays, cell counting etc.

If, in a specific embodiment, a comparison of the determined number and/or size and/or shape of the optically modulating elements, with said predetermined number and/or size leads to a difference, the focus of the reading device may be adjusted and/or the distance between the reading device and the material comprising the optically modulating elements may be modified or adjusted. This may be done automatically, e.g. with the help of electronic or mechanical devices, typically in the form of autofocussing on an object. Suitable techniques, devices, or calculation methods etc. are known to the person skilled in the art. Alternatively, theses parameters may be adjusted manually.

If, in a further specific embodiment, a comparison of the determined number and/or size of the optically modulating elements, with said predetermined number and/or size leads to a difference, additionally or alternatively the exposure time for the detection unit may be adjusted according to the amount and intensity of light reaching the detection unit, e.g. in reaction to the depth of image field, the distance range over which objects are acceptably sharp or in focus or any other suitable parameter known to the person skilled in the art. The adjustment may be carried out automatically, e.g. with the help of electronic or mechanical devices, typically in the form of an automated comparison to a lookup table. Suitable techniques, devices, lookup tables for threshold values etc. are known to the person skilled in the art. Alternatively, the exposure time may be adjusted manually.

In a further embodiment, the chromatic aberration of a detection lens may be determined based on a comparison of the determined number and/or size and/or shape of the optically modulating elements, with said predetermined number and/or size. If, in a further specific embodiment, a comparison of the determined number and/or size of the optically modulating elements, with said predetermined number and/or size leads to a difference, the chromatic aberration of the detection lens may be adjusted.

Alternatively light emission may be determined. For instance the light emission of the optically modulating elements present in the device or system may be determined. A correspondingly obtained value may be compared to a previously obtained and registered value for the light emission. If, in a further specific embodiment, a comparison of the determined light emission of the optically modulating elements, with said predetermined light emission leads to a difference, the focus, the exposure time and/or the chromatic aberration of the detection lens may be adjusted, e.g. as described herein.

The term "difference" as used herein refers to a deviation of more than about 1%, more than about or equal to 2%, more than about or equal to 3%, or more than about or equal to 4%, or more than about or equal to 5%, 6%, 7%, 8%, 9%, 10%, 11%, 12%, 13%, 14%, 15%, 20%, 25%, or 30% deviation between the number and/or size of the optically modulating elements, with said predetermined number and/or or size of said elements.

If in a further embodiment, for example, no optically modulating, geometric element, spot or form is detectable, the device or system and/or any procedure, function or method carried out with or in said device or system may be considered as non-usable.

Alternatively, if, for example, the value indicative for the number of optically modulating elements, spots, or forms is much larger than the predetermined value, i.e. too many optically modulating elements, spots, or forms are detectable, the device or system and/or any procedure, function or method carried out with or in said device system may also be considered as non-usable. Otherwise, i.e. if the value is within a range, e.g. within a range of 1% to about 3%, or within a range of about 1% to 4%, 5%, 6%, 7%, 8%, 9%, 10%, 11%, 12%, 13%, 14%, 15%, 20%, 25%, or 30% deviation between the detected number or size and the predetermined number of size of the elements, the device or system and/or any procedure, function or method carried out with or in said device system may also be considered as usable and/or be confirmed. If a non-usability situation is encountered in this context the usage of the device or system may be discontinued and/or any results obtained may be disregarded. Corresponding information may be recorded electronically or encoded in a barcode or datamatrix or any other suitable coding material. Such a barcode or datamatrix may, for instance, be attached to a device or microfluidic channel.

In a further embodiment the method may additionally comprise positioning a sample supposed to comprise one or more species of particles to be detected in a reaction chamber comprised in the device; and detecting/determining a value indicative for the presence and/or number of one or more species of particles. In a specific embodiment this additional step may be carried out once the usability of the device or system has been shown or confirmed. The detection may be carried out as described herein above.

In one specific embodiment, the method may comprise displacing at least a part of the sample within the reaction chamber. E.g. such a displacement may be carried out with one or more displacers or displacer structures.

In a further embodiment the material comprised in a device, a system or a cartridge as used in a method as described above may comprise an array of optically modulating spots. Such elements may, for example be present as a geometrically ordered array, or be present in the form of a barcode, character or in any other form or shape. The array may, for example, comprise 2 spots, 3, 4, 5, 6, 7, 8, 9, 10, 20, 30, 40, 50, 60, 70, 80, 90, 100, 200, 300, 500, 1000 or more than thousand spots per unit or surface of the device, system or cartridge.

In a further embodiment the material comprised in a device, a system or a cartridge as used in a method as described above is at least partially composed of or comprises material as defined herein above, e.g. plastic material, or combinations of plastic material with other material as defined herein above.

In an embodiment the sample to be analysed as mentioned is a blood sample. In yet another embodiment the blood sample is a sample of human blood.

In an embodiment the particle to be detected as mentioned herein, or to be measured or identified in a method as described above is a prokaryotic cell, eukaryotic cell, or a viral particle. In a specific embodiment, the particle is a human cell. In another specific embodiment, the particle is a T helper cell, e.g. a human T helper cell. In another specific embodiment, the particle is a $CD4^+$ T-cell, e.g. a human $CD4^+$ T-cell.

In an embodiment a cartridge which is partially composed of or comprises material as defined herein above is provided, wherein the cartridge (FIG. 7, Ref. 100) is suitable for the analysis of the number of cells, e.g. the number of T helper cells or of $CD4^+$ T-cells. In a specific embodiment, the cells may be derived from suitable samples, e.g. from a blood sample, in particular a clinical human blood sample.

Figure 7:
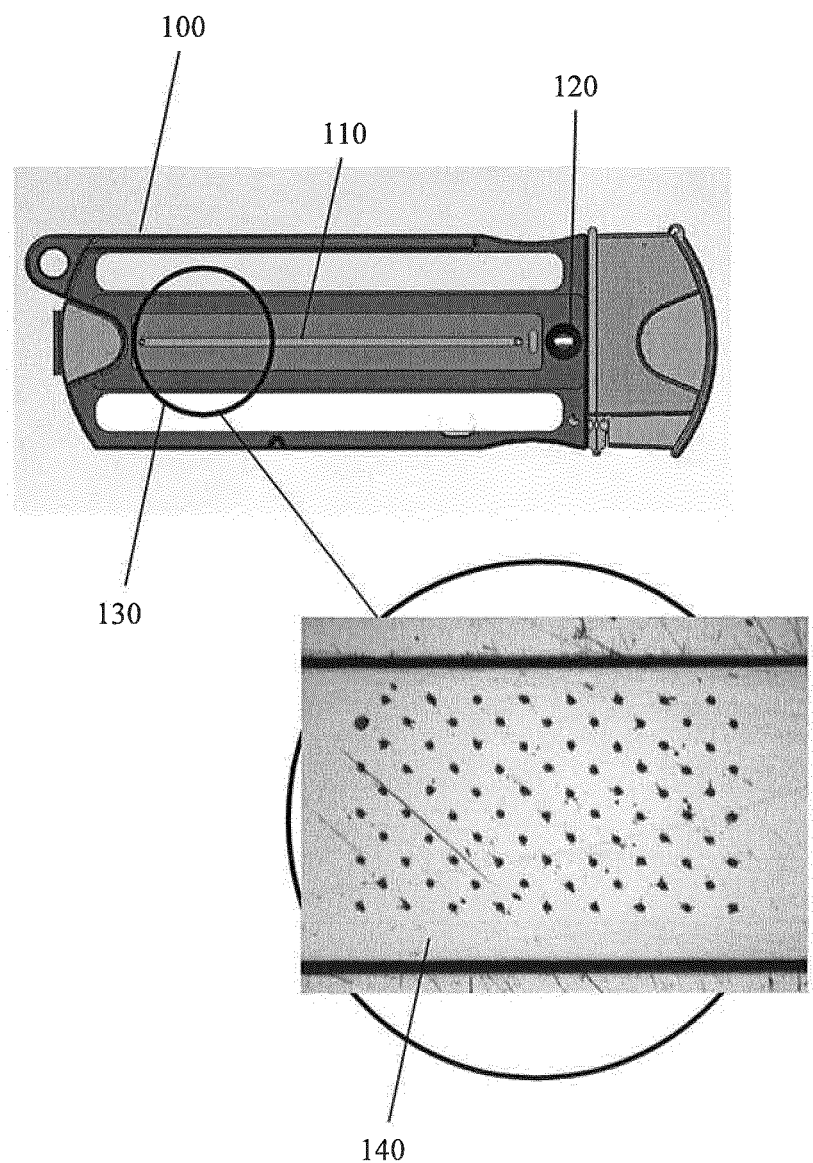
FIG. 7 illustrates a microfluidic cartridge (100) suitable for determining the number of T helper cells in blood, comprising a detection channel (110) and a control for a capillary inlet (120). The figure further shows a section of the detection channel (130), with an array of optically modulating laser spots (140) in an enlarged view.

In one embodiment the cartridge may comprise a detection channel (FIG. 7, Ref. 110). In a specific embodiment the detection channel may comprise control elements for adjusting e.g. the focus position or the exposure time of a detector arranged relative to the detection channel, e.g. in a section of the detection channel (FIG. 7, Ref. 130). In a further specific embodiment the detection channel may comprise control elements for adjusting e.g. the focus position or the exposure time of a detector arranged relative to the detection channel and/or for checking of the chromatic aberration of a detection lens, e.g. in a section of the detection channel (FIG. 7, Ref. 130).

In yet another embodiment the cartridge may further comprise a capillary inlet suitable for the intake of a sample, e.g. a blood sample. In a specific embodiment, the cartridge may as well comprise a control for said capillary inlet (FIG. 7, Ref. 120).

In a further specific embodiment the cartridge may comprise a predetermined range of one or more optically modulating singular spots (FIG. 7, Ref. 140). The optically modulating spots may, in a further embodiment, have a defined geometric shape and specific optically modifying characteristics. In another embodiment the optically modulating spots may be located on each individual cartridge at a defined position in the detection channel, e.g. in a section of the detection channel as depicted in FIG. 7, Ref. 130.

In yet another embodiment the method of transformation of material as described above may be used for the modification or generation of a microfluidic cartridge (FIG. 7, Ref. 100).

In another embodiment a cartridge (FIG. 7, Ref. 100) comprising a detection channel (FIG. 7, Ref. 110), a capillary inlet, a control for a capillary inlet (FIG. 7, Ref. 120), and a predetermined range of one or more optically modulating singular spots having a defined geometric shape and specific optically modifying characteristics (FIG. 7, Ref. 140) located in the detection channel, or a cartridge as defined herein above, may be used for determining a number of cells in a blood sample. The cells to be determined may be any cells. In a specific embodiment, the cells are T helper cells or CD4$^+$ T-cells.

In another embodiment, the determination of the number of cells may include a step of adjusting the focus position or the exposure time of a detector arranged relative to the detection channel, e.g. via control elements. In a particular embodiment, the determination of the number of cells may include a step of adjusting the focus position or the exposure time of a detector arranged relative to the detection channel via control elements such as one or more singular optically modulating spots having a defined geometric shape and specific optically modifying characteristics (FIG. 7, Ref. 140).

In a further embodiment, the determination of the number of cells may include a step of adjusting the focus and exposure time of the detection system and furthermore a check of the chromatic aberration of a detection lens, e.g. via control elements. In a particular embodiment, the determination of the number of cells may include a step of adjusting the focus and exposure time of the detection system and furthermore a check of the chromatic aberration of a detection lens via control elements such as one or more singular optically modulating spots having a defined geometric shape and specific optically modifying characteristics (FIG. 7, Ref. 140).

In yet another embodiment, a correspondingly performed test or assay, e.g. comprising adjustment steps as characterized above, may be considered invalid and/or no test result but an error code may be displayed if a predefined threshold parameter is not reached. E.g. if the focus position or the exposure time of a detector arranged relative to the detection channel controlled via the one or more singular optically modulating spots having a defined geometric shape and specific optically modifying characteristics (FIG. 7, Ref. 140) does not reach the predefined threshold.

Other embodiments are within the scope of the claims.

EXAMPLES

Example 1: Preparation of Colored Dots by a Laser with 1064 nm in Polystyrene FIGS. 2A-B and 3A-B show a regular pattern of structures in a optically modulating state on a plastic surface. For this, a polystyrene plastic part containing 4% carbon black was beneath a 1064 nm laser. The focus plain was adjusted by a standard method measuring the highest impact of the laser beam onto a surface.

Single dots were generated by the laser. Each single pulse of the laser was deviated to an individual position on the surface of the plastic part.

Figure 2:
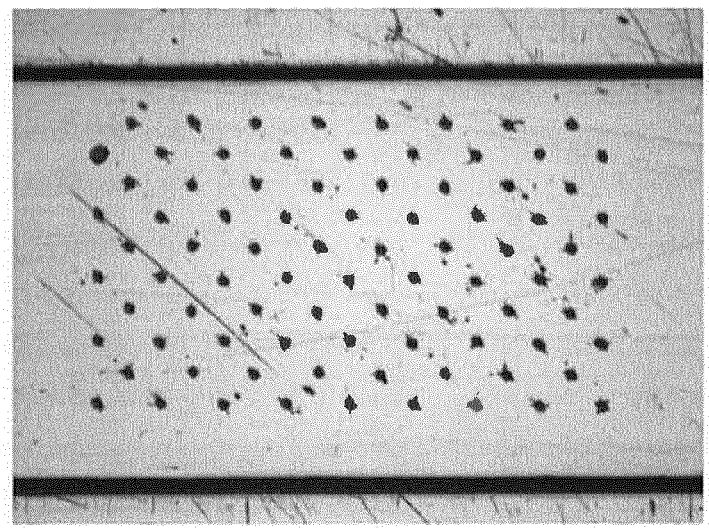
FIG. 2 shows spots generated with a Nd:YAG laser of 8 W power, at a wavelength of 1064 nm, a power of the diodes of 33%, a frequency of pulse of 35 kHz and a pulse width of 5 µs on polystyrene plastic containing 5% carbon black.
Figure 2:
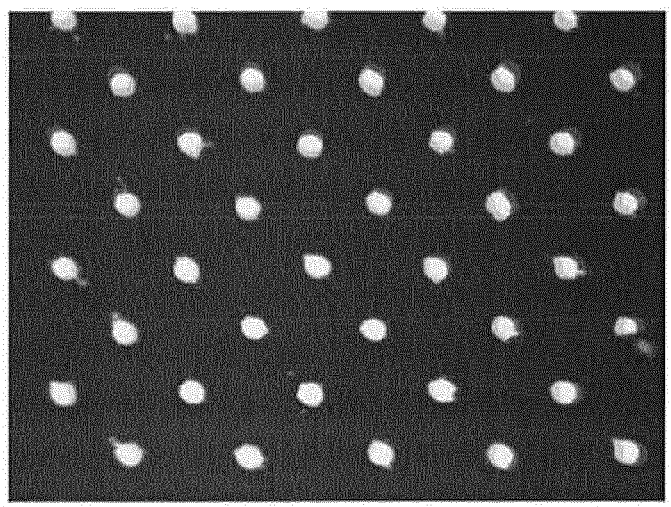
Figure 3:
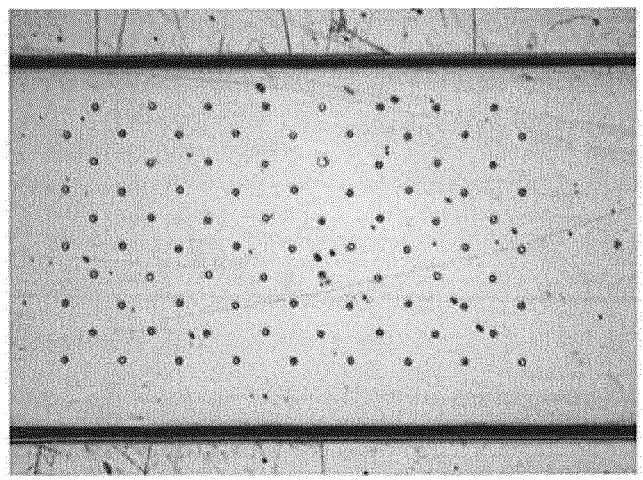
FIG. 3 shows spots generated with a Nd:YAG laser of 8 W power, at a wavelength of 1064 nm, a power of the diodes of 29%, a frequency of pulse of 35 kHz and a pulse width of 5 µs on polystyrene plastic containing 5% carbon black.
Figure 3:
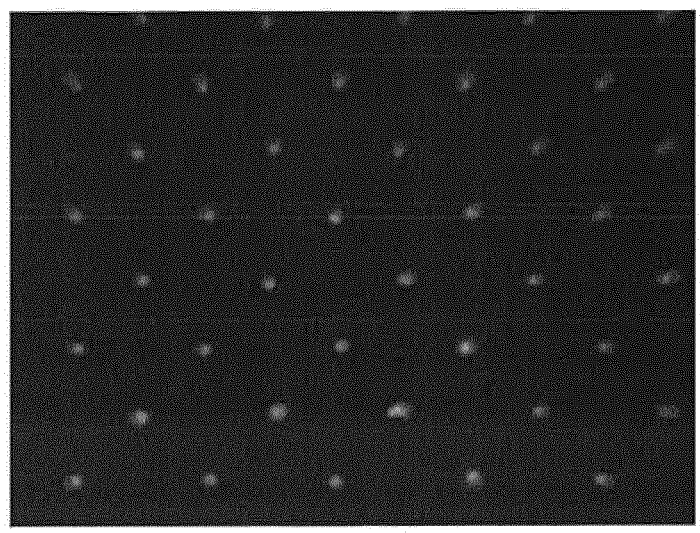

The energy of the pulse can be influenced by the power of the diodes, which are needed to pulse the laser. In addition, the frequency of the laser also influences the energy. A laser pulse having a higher frequency results in a decrease of the energy of the laser beam. FIGS. 2A and 3A show the surface as seen in a standard microscope (Zeiss Axioskop, 10× magnification), FIGS. 2B and 3B as seen in a fluorescence reader (excitation wavelength 520 nm).

For all experiments, a Nd:YAG laser with a maximum power of 8 W and a wavelength: of 1064 nm was used. The frequency of the pulse was adjusted to 35 kHz at a pulse length of 5 µs. For FIGS. 2A and B, the power of the laser diodes was adjusted to 33% of the maximum power, for FIGS. 3A and B the power of the laser diodes was adjusted to 29% of the maximum power.

As can be derived from the figures, a decrease of laser energy results in smaller spots generated on the surface.

Figure 4:
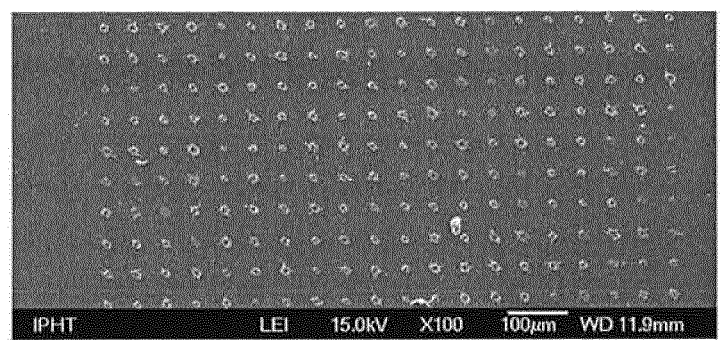
FIG. 4 shows REM images of spots generated by laser radiation emitted from a 355 nm laser at a frequency of 15 kHz on polystyrene plastic containing 5% carbon black.
Figure 4:
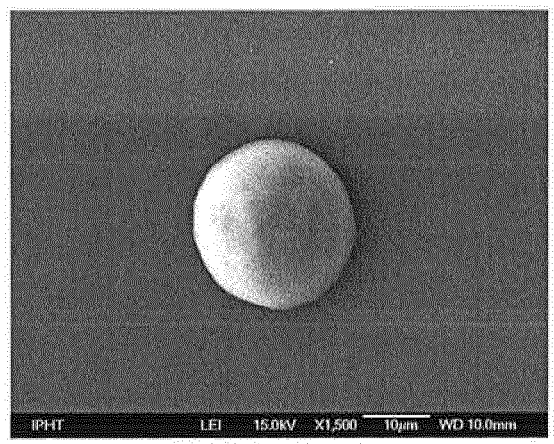
Figure 4:
Figure 4:
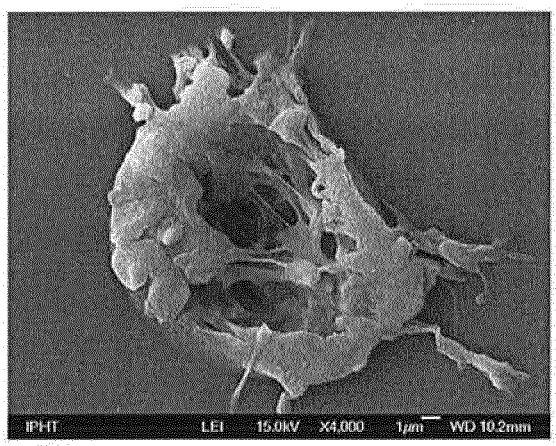
Figure 4:
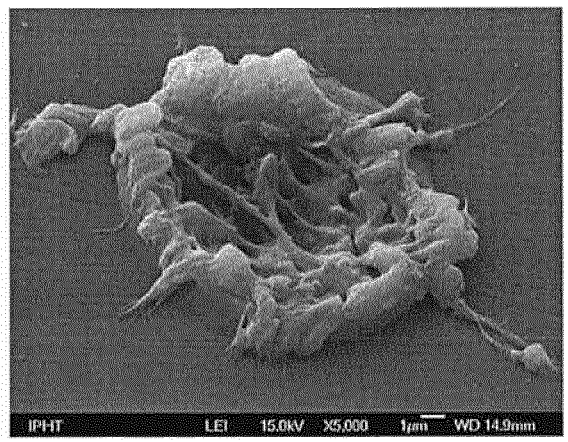

Example 2: Determination of the Morphology of Transformed Material with REM Microscopy Spots having an optically modulating state were generated on PS surface containing 5% carbon black by using a laser with a wavelength of 355 nm, and a frequency of 15 kHz. FIG. 4 A-E show REM pictures of the modifications created on the surface by using different laser energies. It could be shown that the spots' morphology is dependent on the energy applied. At a lower energy, spots appear to have more a spherical structure (see FIGS. 4B and 4C). Higher energy leads to a burst of the spherical structures, as can be seen from FIGS. 4D and 4E). All modifications were detected by using a fluorescence microscope.

Example 3: Correlation Between Signal Intensity and the Power of the Laser

Figure 5:
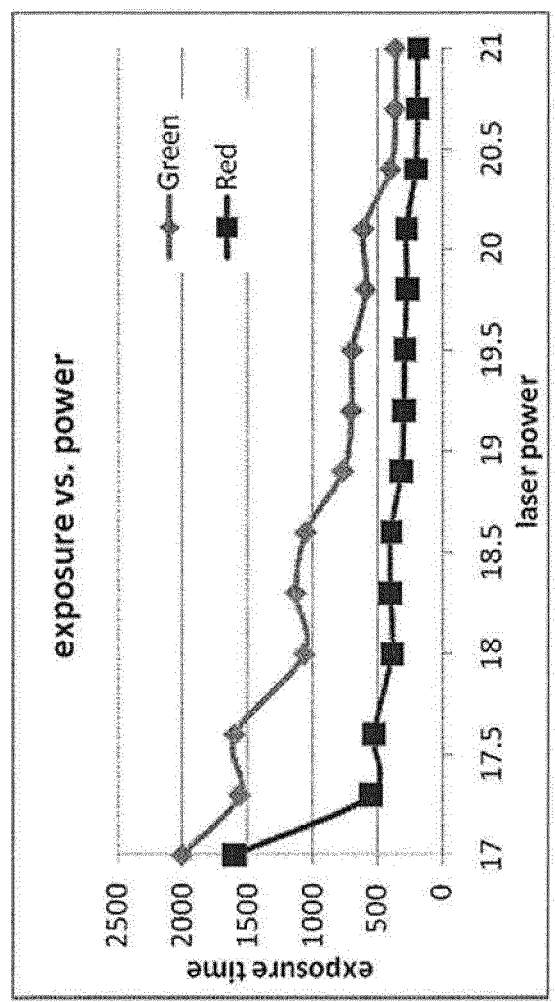
FIG. 5 depicts a correlation between signal intensity and laser power. The intensity of the spots is reflected by the exposure time in the plastic material, correlated with the power of the laser. The green signal corresponds to a wavelength of 593 nm, the red signal was measured at a wavelength of 685 nm. The excitation was done by diode with a peak at 520 nm.

The correlation between the signal intensity and the power of the laser was tested by creating optically modulating spots on a PS surface as described in example using a laser at different adjusted to different energies. The surface was placed in a PIMA reader and the exposure time necessary for generating the same signal strength was measured. The results of this experiment are depicted in the diagram of FIG. 5 showing the relationship between the exposure time [ms] and the laser strength [A]. For low signal intensities, a long exposure time is necessary, for high signal intensities, the exposure time may be shortened. As can be derived from the diagram, a higher laser power results in an increased amount of emitted light.

Example 4: Data Matrix Code Written by the Laser 355 nm on the PS Surface

Figure 6:
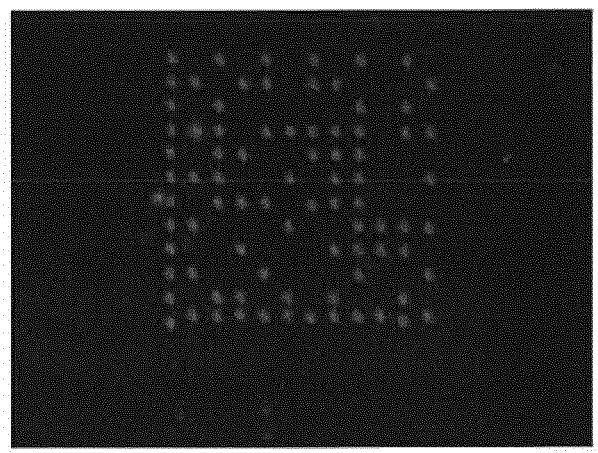
FIG. 6 shows a data matrix code generated by laser radiation emitted from a 355 nm laser at a frequency of 15 kHz on polystyrene plastic containing 5% carbon black. The grid of the dots is 50 µm. The figure depicts the data matrix code illuminated with light of a wavelength of 520 nm. The image was taken by a PIMA analyzer.

It could further be shown that it is possible to use laser radiation in order to write datamatrix code on a PS surface. The laser used was a 355 nm laser with 19.6 A and a frequency of 15 kHz. The results of this approach are depicted in FIG. 6. The grid of the dots of the DMC is 50 µm.

Figure 8:
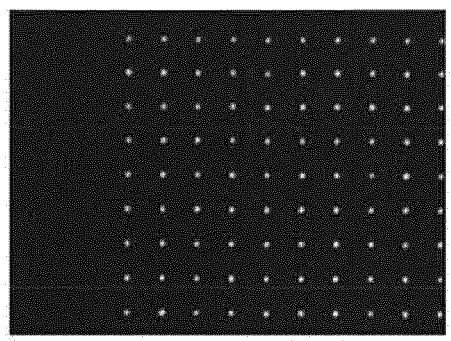
FIG. 8 shows a shifted regular pattern of structures in an optically modulating state on the surface of a channel of a microfluidic device as depicted in FIG. 7. For this, the body of the device made from polystyrene plastic part containing 4% carbon black was treated with a 355 nm Nd:YAG laser.
Figure 8:
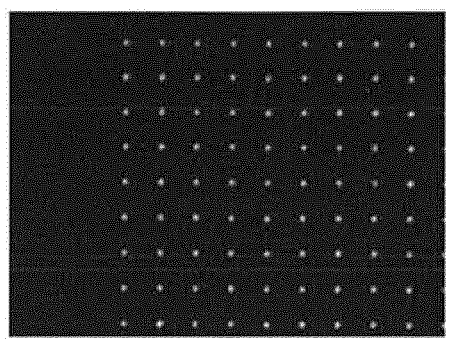

Example 5: Microfluidic Cartridge Comprising Channel with Structures in an Optically Modulating State FIG. 8 shows a shifted regular pattern of structures in an optically modulating state on the surface of a channel of a microfluidic device as depicted in FIG. 7. For this, the body of the device made from polystyrene plastic part containing 4% carbon black was treated with a 355 nm Nd:YAG laser. The focus plain of the laser was adjusted by a standard method measuring the highest impact of the laser beam onto a surface.

On the surface of the channel, single dots were generated by the pulsed laser in a bitmap mode. Each single pulse of the laser was deviated by a galvo system to an individual position on the surface of the plastic part.

The energy of the pulse can be influenced by the power of the diodes, which are needed to pulse the laser. In addition, the frequency of the laser also influences the energy. A laser pulse having a higher frequency usually results in a decrease of the energy of the laser beam. For the experiments, a Nd:YAG laser with a power of 2.1 W and a wavelength of 355 nm was used. The frequency of the pulse was adjusted to 15 kHz at a pulse length of 1.5 µs. Further the power of the laser beam was reduced by an optical instrument by 90%.

FIGS. 8 A and B show the surface of the channel comprising the structures in an optically modulating state imaged by a PIMA Analyzer (Device serial number D-000366, Alere Technologies GmbH). The PIMA Analyzer includes fluorescent microscope functionality and has the capability to detect fluorescent signals at defined wavelengths, e.g. 593 nm and 685 nm while the excitation light is removed from detection by using filter elements. The system software allows varying the exposure time and master gain within a certain range. The master gain factor is multiplying the signal taken with camera with a defined factor.

FIGS. 8A and 8B show the structures in a optically modulating state excited at a standard excitation wavelength of the PIMA system at 520 nm. In FIG. 8A, the image was detected at a wavelength of 593 nm and an exposure time of 300 ms and a master gain of 2.74, while the image shown in FIG. 8B was detected at 685 nm with a exposure time of 300 ms and a master gain factor of 11.68.

In both images, the structures in an optically modulating state on the surface of the channel of the microfluidic device can be detected at a wavelength different to the excitation wavelength.

As previously described herein, the structure can be used to adjust and or control e.g. the focus position and/or the exposure time of the detection system of the PIMA system. And/or, as described herein, the structures can be used to serve as an internal control for assessing the validity of the experiment results.

The invention claimed is:

1. A method of calibrating an optical reader comprising providing a cartridge comprising a plastic material, the plastic material having a surface modified by applying laser radiation to form a reference mark transformed into an optically modulating state upon excitation, emitting light in a wavelength spectrum of about 550 nm to about 880 nm,
positioning an optical reader capable of detecting light emitted from the one or more reference marks, and
detecting, with the optical reader, light emitted by the reference marks upon excitation.

2. The method of claim 1, wherein, upon excitation, said one or more reference marks emit light at peak wavelengths of 593 nm and/or 685 nm.

3. The method of claim 1 wherein said excitation is a broadband light excitation.

4. The method of claim 3, wherein said broadband light excitation is an excitation in a wavelength spectrum of about 380 nm to about 540 nm and/or a wavelength spectrum of about 635 nm to about 655 nm.

5. The method of claim 1, wherein said plastic material is a thermoplastic material or an elastomeric material.

6. The method of claim 1, wherein said plastic material is an organic polymer selected from the group consisting of polyethylene, polypropylene, polystyrene, polycarbonate and polycycloolefin.

7. The method of claim 1, further comprising validating the optical reader.

* * * * *